(12) United States Patent
Block et al.

(10) Patent No.: US 12,194,298 B2
(45) Date of Patent: Jan. 14, 2025

(54) SYSTEMS AND METHODS FOR SELECTABLE LATERAL SPINAL CORD STIMULATION

(71) Applicant: Boston Scientific Neuromodulation Corporation, Valencia, CA (US)

(72) Inventors: Jessica Block, Sherman Oaks, CA (US); Rosana Esteller, Santa Clarita, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 389 days.

(21) Appl. No.: 17/589,738

(22) Filed: Jan. 31, 2022

(65) Prior Publication Data
US 2022/0241593 A1 Aug. 4, 2022

Related U.S. Application Data

(60) Provisional application No. 63/144,387, filed on Feb. 1, 2021.

(51) Int. Cl.
*A61N 1/36* (2006.01)
*A61N 1/05* (2006.01)
*A61N 1/372* (2006.01)

(52) U.S. Cl.
CPC ....... *A61N 1/36071* (2013.01); *A61N 1/0551* (2013.01); *A61N 1/37241* (2013.01); *A61N 1/37247* (2013.01)

(58) Field of Classification Search
CPC .............. A61N 1/0551; A61N 1/36071; A61N 1/36132; A61N 1/37241; A61N 1/37247
See application file for complete search history.

(56) References Cited

U.S. PATENT DOCUMENTS

| | | | |
|---|---|---|---|
| 9,984,209 B2 | 5/2018 | Cerny et al. | |
| 10,076,667 B2* | 9/2018 | Kaula | G16H 20/30 |

(Continued)

FOREIGN PATENT DOCUMENTS

| | | |
|---|---|---|
| CN | 116887885 A | 10/2023 |
| WO | WO-2022165376 A1 | 8/2022 |

OTHER PUBLICATIONS

"European Application Serial No. 22704479.9, Response to Communication pursuant to Rules 161 and 162 filed Mar. 6, 2024", 13 pgs.

(Continued)

*Primary Examiner* — George Manuel
(74) *Attorney, Agent, or Firm* — Schwegman Lundberg & Woessner, P.A.

(57) ABSTRACT

Systems and methods for selectable lateral spinal cord stimulation are discussed. An exemplary neuromodulation system includes a programming device and an electrostimulator. The programming device can receive information about placement of at least one lead in a vicinity of a lateral portion of a spinal cord, identify one or more lateral spinal neural targets based on the information about placement of the at least one lead, and receive a user selection from selectable stimulation modes for stimulating the identified one or more lateral spinal neural targets. The electrostimulator can apply electrostimulation energy to the identified one or more lateral spinal neural targets via the at least one lead in accordance with the user selection from the selectable stimulation modes.

18 Claims, 28 Drawing Sheets

(56) References Cited

U.S. PATENT DOCUMENTS

| | | |
|---|---|---|
| 10,272,247 B2* | 4/2019 | Bokil ................ G16H 50/50 |
| 10,675,469 B2* | 6/2020 | Annoni ............. A61N 1/36139 |
| 2012/0296392 A1 | 11/2012 | Lee et al. |
| 2013/0060299 A1 | 3/2013 | Polefko et al. |
| 2015/0119958 A1 | 4/2015 | Li et al. |
| 2016/0220823 A1 | 8/2016 | Ranu |
| 2019/0366096 A1 | 12/2019 | Torgerson |

OTHER PUBLICATIONS

"International Application Serial No. PCT/US2022/014622, International Preliminary Report on Patentability mailed Aug. 10, 2023", 8 pgs.

"International Application Serial No. PCT/US2022/014622, International Search Report mailed Apr. 26, 2022", 4 pgs.

"International Application Serial No. PCT/US2022/014622, Written Opinion mailed Apr. 26, 2022", 6 pgs.

"Australian Application Serial No. 2022213430, First Examination Report mailed May 10, 2024", 3 pgs.

* cited by examiner

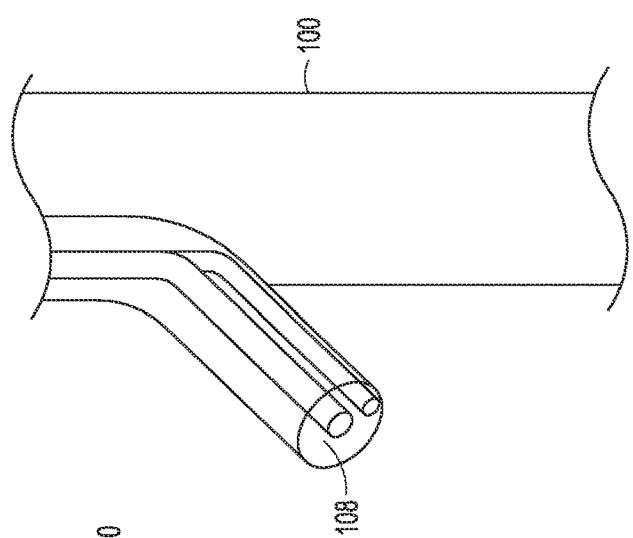
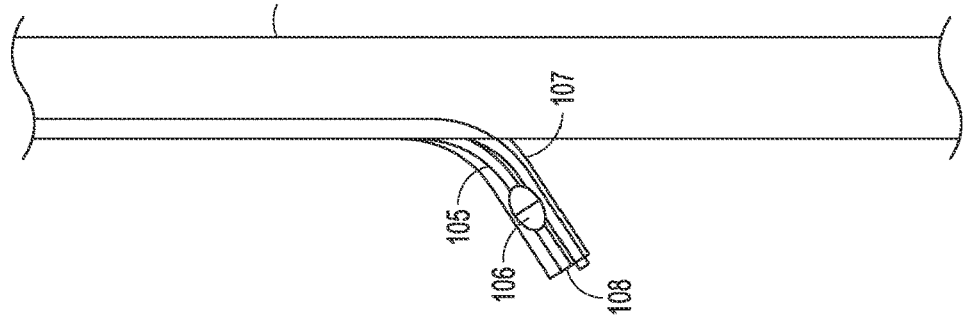
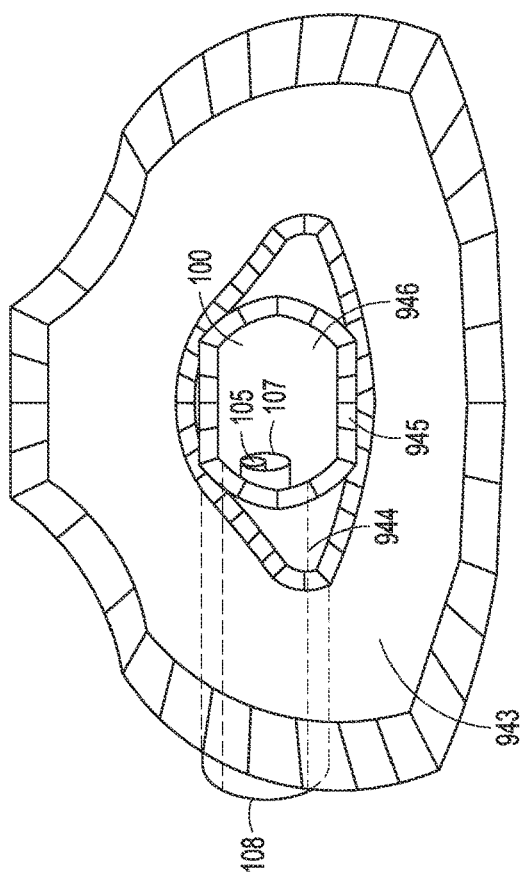

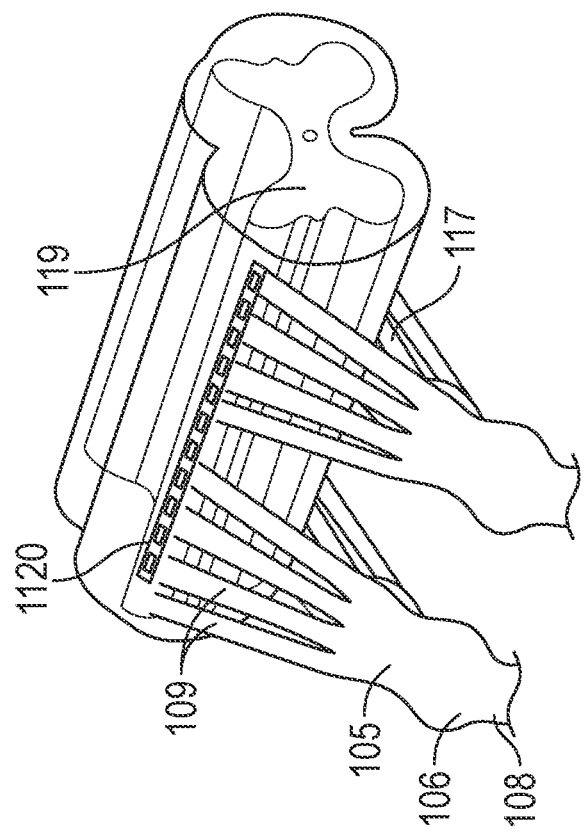
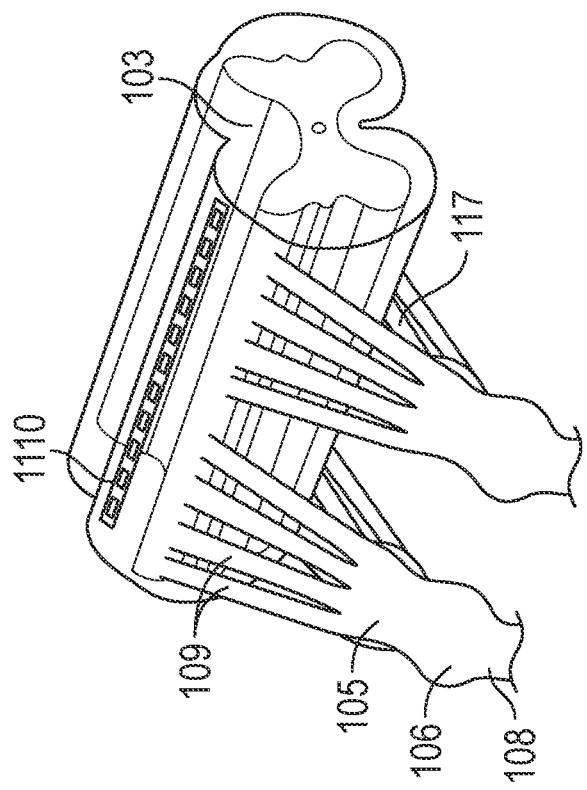

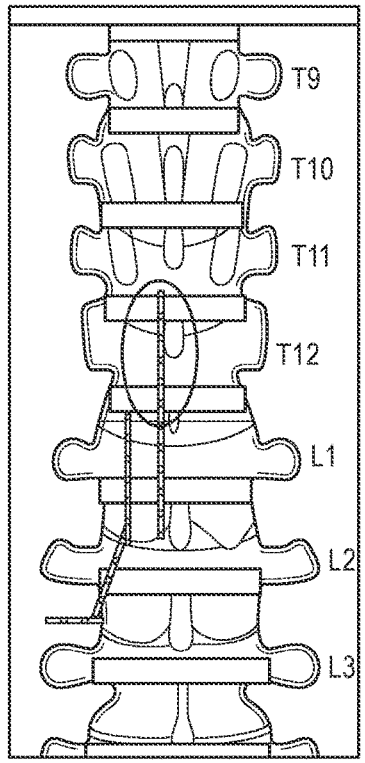

3. Walk through Contact Groups

3a. Paresthesia-Based — 1622

| Paresthesia-Based: | Anodic (focal) | v |

- Bipole Mode
- Illumina Steering
- Sensations

1623 — Programming Screen Updated Based on Feeling-Based Selection

Pulse Width: 40 — 340
Rate: 40 — 150
Modulation Depth: 10 — 90
Modulation Frequency: 1 — 5

3b. Paresthesia-Free — 1624

| Paresthesia-Free: | • FAST | v |

- Microburst
- DHM

1625 — Programming Screen Updated Based on Silent-Based Selection

Targets of Interest — 1621
○ Dorsal Column
○ Dorsal Horn
○ DREZ
○ Rootlets
○ Dorsal Roots

[ Next Target ]  [ Next Contact Group ]

FIG. 16B

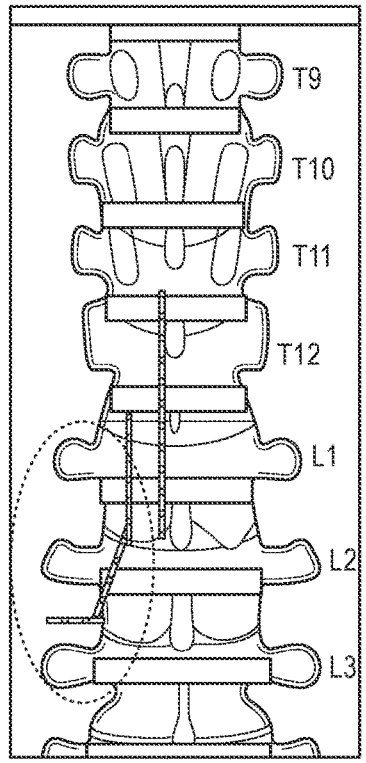

3. Walk through Rest of Contact Groups

3a. Feeling-Based — 1642

| Feeling-Based: | • Bipole Mode V |

• Illumina Steering

• Sensations

1643 — Programming Screen Updated Based on Feeling-Based Selection

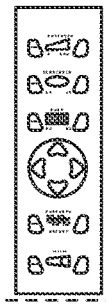

3b. Silent-based — 1644

| Silent-Based: | • FAST V |

• Microburst

• DHM

Targets of Interest
- Dorsal Column
- Dorsal Horn
- DREZ
- Rootlets
- Dorsal Roots

1641

1645 — Programming Screen Updated Based on Silent-Based Selection

Next Target | Next Contact Group

FIG. 16D

SYSTEMS AND METHODS FOR SELECTABLE LATERAL SPINAL CORD STIMULATION

CLAIM OF PRIORITY

This application claims the benefit of priority of U.S. Provisional Patent Application No. 63/144,387, filed Feb. 1, 2021, which is herein incorporated by reference in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Some neural targets may be complex structures with different types of nerve fibers. An example of such a complex structure is the neuronal elements in and around the spinal cord targeted by SCS. This complexity may contribute to difficulties in placing modulation electrodes and difficulties in programming the modulation field(s) in different patients as the optimal placement of the modulation electrodes and the optimal modulation field to treat a specific pain area can vary among patients. Although physicians may guide the lead only using the bony anatomy detected by fluoroscopy, they are unable to accurately determine the underlying nerve structures (neuroanatomy) for a specific patient from the fluoroscopic image.

Lateral stimulation of nerve fibers innervating the spinal cord may be used to target focal pain such as pain focused in a foot, a knee, or a hip. Such lateral stimulation may be provided by a technique using epidural mid-line leads that target the dorsal columns. The implantation of the mid-line epidural leads is a relatively easy surgical procedure without need of specialized surgical training for the physician. However, the mid-line epidural leads may or may not provide the desired coverage of the focal pain area, and may or may not provide stimulation spill over. Furthermore, it can be challenging to find settings to cover both low back and focal pain. In another technique, epidural leads may be placed to target the dorsal root ganglion (DRG). This approach may provide good focal pain coverage. However, the surgical procedure is more complex (e.g. complex steering) which may require specialized training for the physician. Furthermore, a small therapeutic window for stimulating the DRG may result in over stimulation. Yet another technique uses peripheral nerve stimulation, which can provide good focal pain coverage. However, the surgical procedure is more complex in order to access a targeted peripheral nerve and secure the lead placement. Peripheral nerve stimulation may also be more likely to stimulate motor axons along with the sensory axons.

Therefore, there is a need for other, more effective options for spinal cord lateral stimulation to treat focal pain.

SUMMARY

Various embodiments discussed in this document may provide more effective lateral stimulation of the spinal cord by targeting lateral spinal neural targets such as dorsal roots, dorsal rootlets, or a Dorsal Root Entry Zone (DREZ), over other neural targets such as the DRG, ventral roots or spinal nerve roots. Systems and methods are provided to guide programming, by a user (e.g., a physician), for leads placed epidurally, foraminally, or through the sacral hiatus. Various embodiments may identify lateral spinal neural targets corresponding to the epidural leads placement and focal pain areas, and automatically populate a selectable set of therapy options (e.g., electrode configurations for neurostimulation). By selectively or preferentially targeting sensory fibers in a dorsal root, dorsal rootlets, or the DREZ to treat focal pain, the system may be able to avoid the undesirable effects of stimulating DRGs, ventral roots or spinal nerve roots. Lateral placement of leads placed through the epidural space (hereinafter referred to as "epidural leads") targeting these lateral neural targets may also simplify the surgical procedure. For example, the lateral placement of epidural leads as discussed in this document does not require the lead be placed outside foramen, as long as the most distal lead contact is at the area of foramen. Neither is the lead required to be placed below conus medullaris because this targets the terminals of the roots at the entrance to the spinal cord.

The following examples illustrate various aspects of the embodiments described herein.

Example 1 is a system for providing spinal cord electrostimulation for pain control in a patient. The system comprises; a programming device configured to; receive information about placement of at least one lead in a vicinity of a lateral portion of a spinal cord; identify one or more lateral spinal neural targets based on the information about placement of the at least one lead; and receive a user selection from selectable stimulation modes for stimulating the identified one or more lateral spinal neural targets; and an electrostimulator configured to apply electrostimulation energy to the identified one or more lateral spinal neural targets via the at least one lead in accordance with the user selection from the selectable stimulation modes.

In Example 2, the subject matter of Example 1 optionally includes the one or more lateral spinal neural targets that can include at least one of a dorsal root entry zone, a Lissauer's track, a dorsal root, or dorsal rootlets.

In Example 3, the subject matter of any one or more of Examples 1-2 optionally includes the selectable stimulation modes that can include at least one of: a monopolar stimulation mode; a bipolar stimulation mode; a tripolar stimulation mode; a steering mode; a sensations mode; a rotation mode; a fast-acting sub-perception therapy mode; a dorsal horn modulation mode; a burst mode; or a low-rate active recharge mode.

In Example 4, the subject matter of any one or more of Examples 1-3 optionally includes the placement of at least one lead that can include a user selection from two or more of a cylindrical lead, a paddle lead, a directional lead, or a curved lead comprising two or more cascaded lead segments arranged at angles relative to each other.

In Example 5, the subject matter of any one or more of Examples 1-4 optionally includes the programming device that can be configured to identify the one or more lateral spinal neural targets, including: generate one or more contact groups each comprising lead electrode-tissue contacts on the lateral portion of spinal cord of the patient; and identify, for each of the one or more contact groups, one or more lateral spinal neural targets.

In Example 6, the subject matter of Example 5 optionally includes the one or more lateral spinal neural targets that can include at least one of: first lateral spinal neural targets, identified for a first contact group, including dorsal column, dorsal rootlets, a dorsal root entry zone, a Lissauer's track, and inhibitory interneurons; second lateral spinal neural targets, identified for a second contact group, including one or more midline dorsal roots; or third lateral spinal neural targets, identified for a third contact group, including one or more lateral dorsal roots.

In Example 7, the subject matter of any one or more of Examples 5-6 optionally includes the programming device that can be configured to: receive information about pain area on patient body, the pain area corresponding to one or more dermatomes; and identify one or more lateral spinal neural targets for a contact group further based on a rostral-caudal position or a medio-lateral position of the contact group relative to spinal cord levels innervating the one or more dermatomes corresponding to the pain area.

In Example 8, the subject matter of any one or more of Examples 5-7 optionally includes the selectable stimulation modes that can include, for each of the one or more contact groups, one or more candidate paresthesia-based stimulation modes and one or more candidate paresthesia-free stimulation modes.

In Example 9, the subject matter of any one or more of Examples 5-8 optionally includes the programming device that can be configured to: for each of the one or more contact groups, receive a user selection from candidate spinal neural targets; and provide selectable stimulation modes for the user selected candidate spinal neural target.

In Example 10, the subject matter of Example 9 optionally includes the candidate spinal neural targets that can include one or more of: a dorsal column; a dorsal horn; a Lissauer's track; a dorsal root entry zone; dorsal rootlets; or a dorsal root.

In Example 11, the subject matter of any one or more of Examples 9-10 optionally includes the selectable stimulation modes that can include, for each of the candidate spinal neural targets, one or more candidate paresthesia-based stimulation modes and one or more candidate paresthesia-free stimulation modes.

In Example 12, the subject matter of any one or more of Examples 1-11 optionally includes: the electrostimulator that can be configured to apply test electrostimulation energy to two or more identified lateral spinal neural targets individually and independently in accordance with corresponding stimulation modes respectively selected for the two or more identified lateral spinal neural targets; and the programming device that can be configured to select one of the two or more identified lateral spinal neural targets based on a patient feedback on pain relief responsive to the electrostimulation individually and independently applied to the two or more identified lateral spinal neural targets; wherein the electrostimulator is configured to apply clinical electrostimulation energy to the selected neural target in accordance with a corresponding stimulation mode.

In Example 13, the subject matter of Example 12 optionally includes a display configured to display the two or more identified lateral spinal neural targets and the stimulation modes respectively selected for the two or more identified lateral spinal neural targets, wherein the programming device is configured to receive a user selection of one of the two or more identified lateral spinal neural targets based on the patient feedback on pain relief responsive to the electrostimulation individually and independently applied to each of the two or more identified lateral spinal neural targets.

In Example 14, the subject matter of any one or more of Examples 1-13 optionally includes the programming device that can be configured to receive the user selection from the selectable stimulation modes including two or more stimulation modes to be applied to respective two or more electrode sets of the at least one lead to stimulate respective two or more lateral spinal neural targets.

In Example 15, the subject matter of Example 14 optionally includes the user selection of the two or more stimulation modes that can include a monopolar anodic stimulation mode applied to a first electrode set to stimulate a dorsal root entry zone at a spinal cord level, and a bipolar stimulation mode applied to a second electrode set to stimulate a dorsal column or a dorsal root at the spinal cord level.

Example 16 is a non-transitory machine-readable storage medium that includes instructions that, when executed by one or more processors of a machine, cause the machine to perform operations comprising: receiving information about placement of at least one lead in a vicinity of a lateral portion of a spinal cord of a patient, identifying one or more lateral spinal neural targets based on the information about placement of the at least one lead; receiving a user selection from selectable stimulation modes for stimulating the identified one or more lateral spinal neural targets; and applying electrostimulation energy to the identified one or more lateral spinal neural targets via the at least one lead in accordance with the user selection from the selectable stimulation modes.

In Example 17, the subject matter of Example 16 optionally includes, wherein the one or more lateral spinal neural targets include at least one of a dorsal root entry zone, a Lissauer's track, a dorsal root, or dorsal rootlets.

In Example 18, the subject matter of any one or more of Examples 16-17 optionally includes, wherein the operation of identifying the one or more lateral spinal neural targets includes: generating one or more contact groups each comprising lead electrode-tissue contacts on the lateral portion of spinal cord of the patient, and identifying, for each of the one or more contact groups, one or more lateral spinal neural targets.

In Example 19, the subject matter of Example 18 optionally includes, wherein the instructions cause the machine to perform operations further comprising receiving information about pain area on patient body, the pain area corresponding to one or more dermatomes, and wherein the operation of identifying one or more lateral spinal neural targets for a contact group is further based on a rostral-caudal position or a medio-lateral position of the contact group relative to spinal cord levels innervating the one or more dermatomes corresponding to the pain area.

In Example 20, the subject matter of any one or more of Examples 16-19 optionally include, wherein the selectable stimulation modes include one or more candidate paresthesia-based stimulation modes and one or more candidate paresthesia-free stimulation modes.

In Example 21, the subject matter of any one or more of Examples 16-20 optionally include, wherein the instructions cause the machine to perform operations further comprising: applying test electrostimulation energy to two or more identified lateral spinal neural targets individually and independently in accordance with corresponding stimulation modes respectively selected for the two or more identified lateral spinal neural targets; selecting one of the two or more identified lateral spinal neural targets based on a patient feedback on pain relief responsive to the electrostimulation individually and independently applied to the two or more identified lateral spinal neural targets; and applying clinical electrostimulation energy to the selected neural target in accordance with a corresponding stimulation mode.

Example 22 is a method for providing spinal cord electrostimulation for pain control in a patient. The method comprises steps of: receiving information about placement of at least one lead in a vicinity of a lateral portion of a spinal cord; identifying one or more lateral spinal neural targets based on the information about placement of the at least one lead using a programming device; receiving a user selection from selectable stimulation modes for stimulating the identified one or more lateral spinal neural targets; and applying electrostimulation energy generated by an electrostimulator to the identified one or more lateral spinal neural targets via the at least one lead in accordance with the user selection from the selectable stimulation modes.

In Example 23, the subject matter of Example 22 optionally includes identifying the one or more lateral spinal neural targets that can include: generating one or more contact groups each comprising lead electrode-tissue contacts on the lateral portion of spinal cord of the patient; and identifying, for each of the one or more contact groups, one or more lateral spinal neural targets including at least one of: first lateral spinal neural targets, identified for a first contact group, including dorsal column, dorsal rootlets, a dorsal root entry zone, a Lissauer's track, and inhibitory interneurons; second lateral spinal neural targets, identified for a second contact group, including one or more midline dorsal roots; or third lateral spinal neural targets, identified for a third contact group, including one or more lateral dorsal roots.

In Example 24, the subject matter of Example 23 optionally includes receiving information about pain area on patient body, the pain area corresponding to one or more dermatomes, wherein identifying one or more lateral spinal neural targets for a contact group is further based on a rostral-caudal position or a mediolateral position of the contact group relative to spinal cord levels innervating the one or more dermatomes corresponding to the pain area.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 9A-9C illustrate a transverse top view, a coronal side view and an angled view, respectively, of a nerve root.

FIGS. 11A-11B illustrate, by way of example, epidural leads placement.

FIGS. 16A-16D illustrate, by way of example, a user interface for programming selectable lateral SCS for pain control.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Figure 1A:
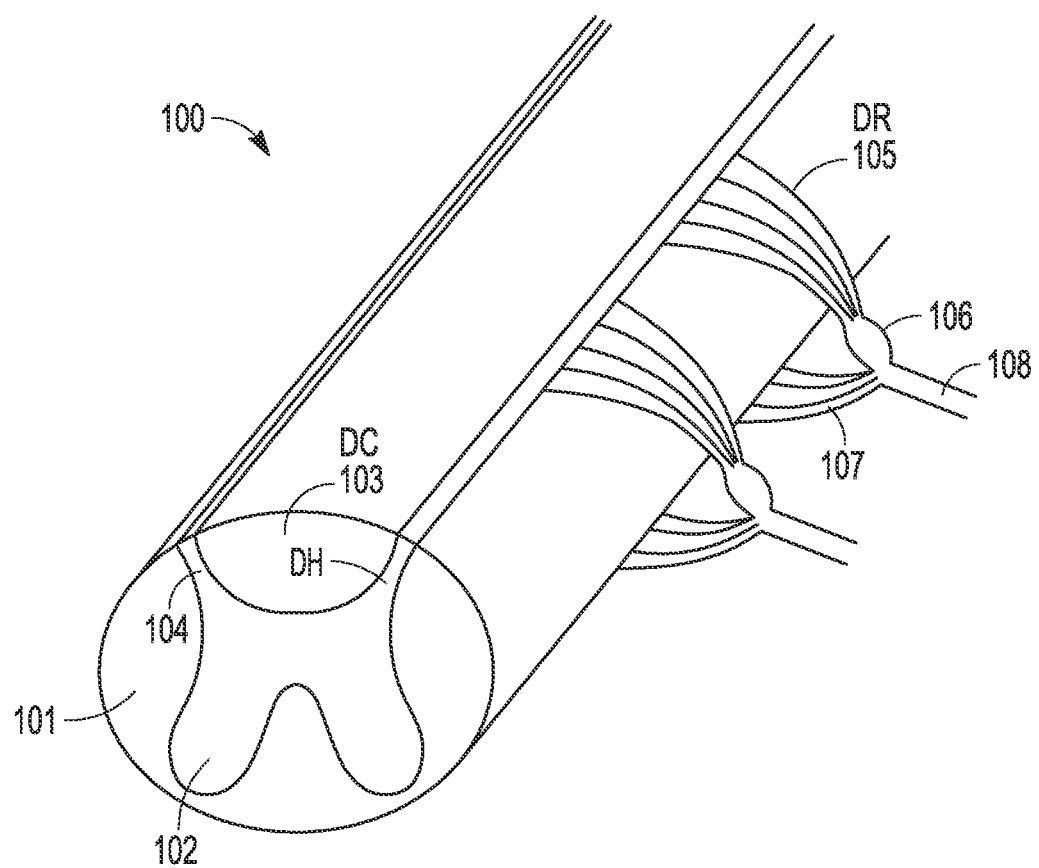
FIGS. 1A-1B illustrate a portion of a spinal cord.
Figure 1B:
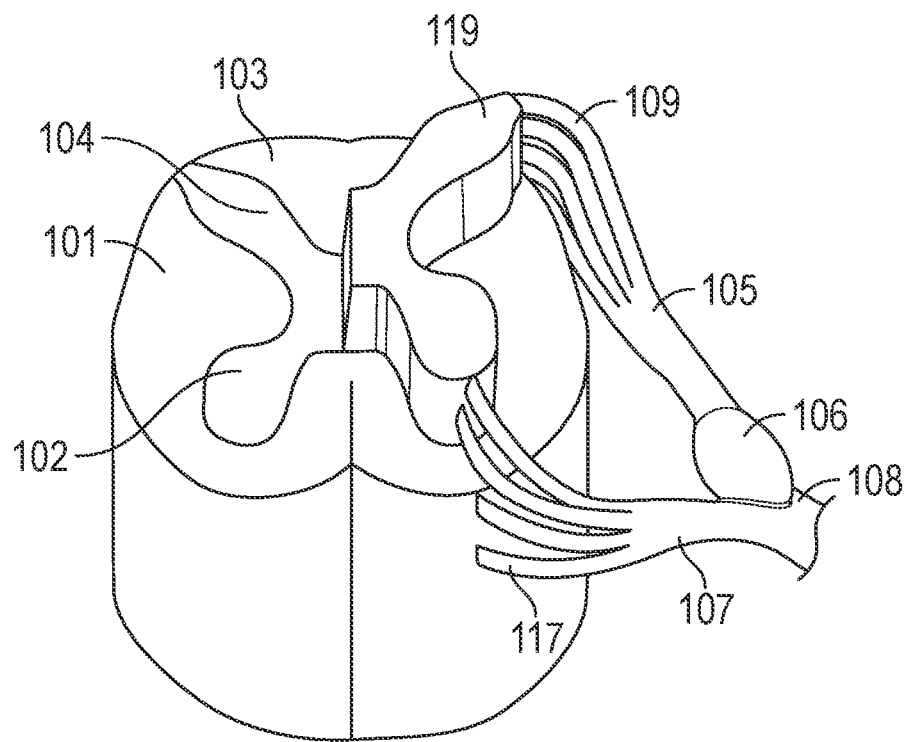

Various embodiments described herein involve spinal cord modulation. A brief description of the physiology of the spinal cord is provided herein to assist the reader. FIGS. 1A-1B illustrate, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. FIGS. 1A-1B also illustrate spinal nerves, including a dorsal root (DR) 105, dorsal rootlets 109, dorsal root ganglion (DRG) 106, ventral root 107, and ventral rootlets 117. The dorsal root 105 mostly carries sensory signals into the spinal cord via a Dorsal Root Entry Zone (DREZ) 119 of the DH 104, and the ventral root 107 functions as an efferent motor root mostly carrying motor signals out of the spinal cord. The dorsal and ventral roots join to form mixed spinal nerve root 108.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

The present subject matter provides systems and methods to selectively or preferentially stimulate DR tissue over other neural tissue, such as but not limited to dorsal roots, dorsal rootlets, DRG, DREZ, or Lissauer's track. A lead or leads, including a plurality of electrodes, may be positioned to place the plurality of electrodes in proximity to a targeted nerve root. For example, the electrodes may be placed adjacent to the targeted nerve root, dorsal rootlets, or DREZ. The lead(s) may be placed using surgical approaches such as a lateral anterograde approach, a lateral retrograde approach, a sacral hiatus approach, or a transgrade approach. The lateral anterograde approach inserts the lead epidurally lower than the target, and then advances the lead in an anterograde direction (toward the head) until the lead is at the targeted nerve root. The lateral retrograde approach may be used to pass the lead closer to the DRG for selective root stimulation by inserting the lead epidurally above the target, and then advancing the lead in a retrograde direction (away from the head) to the targeted nerve root. The sacral hiatus approach introduces the introducer needle through the sacral hiatus into the epidural space and advanced in an anterograde direction (toward the head) to the targeted nerve root. Upon reaching the targeted nerve, the lead may be steered through the foramen to position extraforaminal, foraminal, and intraspinal electrodes along the targeted nerve root. The transgrade approach accesses the contralateral interlaminar space and steers the lead out of the opposite foramen to position extraforaminal, foraminal, and intraspinal electrodes along the targeted nerve root.

Stimulation of DR tissue may be useful to treat focal pain as it may provide the desired coverage for the pain without the stimulation spill over that can cause undesired effects in other areas of the body. Stimulation of DR tissue may be useful for delivering sub-perception therapy, which avoids the paresthesia that accompanies conventional SCS therapy when the large sensory DC nerve fibers are activated. Patients sometimes report these sensations to be unwanted. Sub-perception therapy may effectively treat pain without the patient sensing the delivery of the modulation field (e.g. paresthesia). Selective modulation of DR tissue, for either sub-perception therapy or to treat focal pain, may be delivered at higher frequencies (e.g. over 1,500 Hz such as frequencies within a range of 2 kHz to 20 kHz) or may be delivered at lower frequencies (e.g. at or less than 1,500 Hz such as frequencies at or less than 1,200 Hz, frequencies at or less than 1,000 Hz, frequencies at or less than 500 Hz, frequencies at or less than 350 Hz, or at or less than 130 Hz. The selective modulation may be delivered at low frequencies (e.g. as low as 2 Hz) or may be delivered even without pulses (e.g. 0 Hz). By way of example and not limitation, the selective modulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective modulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle. Some waveforms may combine lower frequency pulses and higher frequency pulses into a more complex waveform (e.g. bursts of higher frequency pulses interleaved between one or more pulses delivered at a lower frequency. The waveform may have a regular pattern of pulses that repeats at regular intervals between pulses or regular intervals between burst of pulses. The waveform may have an irregular pattern of pulse that includes different intervals between pulses and/or different intervals between burst of pulses. The waveform may comprise rectilinear pulses, or may include other morphological shapes that are not rectilinear.

Figure 2:
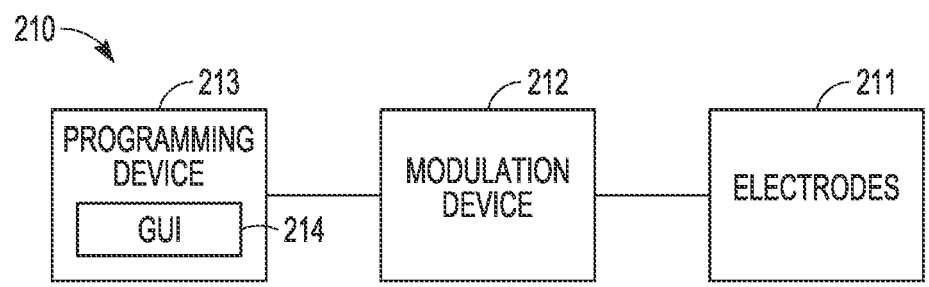
FIG. 2 illustrates, by way of example, an embodiment of a neuromodulation system.

FIG. 2 illustrates an embodiment of a neuromodulation system. The illustrated system 210 includes electrodes 211, a modulation device 212, and a programming device 213. The electrodes 211 are configured to be placed on or near one or more neural targets in a patient, such as one or more dorsal nerve roots. The modulation device 212 is configured to be electrically connected to electrodes 211 and deliver neuromodulation energy, such as in the form of electrical pulses or other waveform shape, to the one or more neural targets though electrodes 211. The modulation device 212 may be an implantable device or an external device with leads percutaneously inserted to be positioned to stimulate a dorsal root. The delivery of the neuromodulation is controlled by using a plurality of modulation parameters, such as modulation parameters specifying the electrical pulses and a selection of electrode(s) to function as anode(s) and a selection of electrode(s) to function as cathode(s) through which each of the electrical pulses is delivered. The modulation parameter may also include the fractional distribution of energy (e.g. current) provided across the anodic electrode (s) and cathodic electrode(s). In various embodiments, at least some parameters of the plurality of modulation parameters are programmable by a user, such as a physician or other caregiver. The programming device 213 provides the user with accessibility to the user-programmable parameters. In various embodiments, the programming device 213 is configured to be communicatively coupled to modulation device via a wired or wireless link. In various embodiments, the programming device 213 includes a graphical user interface (GUI) 214 that allows the user to set and/or adjust values of the user-programmable modulation parameters.

Figure 3:
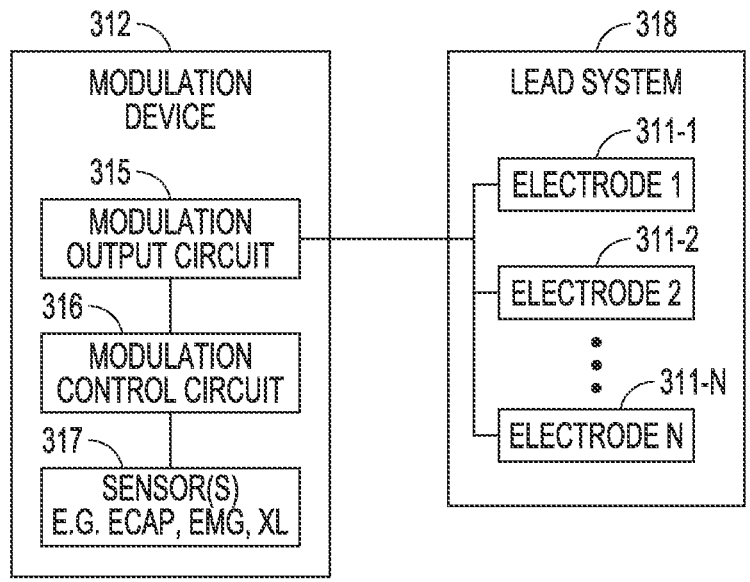
FIG. 3 illustrates, by way of example, an embodiment of a modulation device, such as may be implemented in the neuromodulation system of FIG. 2.

FIG. 3 illustrates an embodiment of a neuromodulation device 312, such as may be implemented in the neuromodulation system 210 of FIG. 2. The illustrated embodiment of the neuromodulation device 312 includes a neuromodulation output circuit 315 and a neuromodulation control circuit 316. Those of ordinary skill in the art will understand that the neuromodulation device 312 may include additional components such as sensing circuitry for patient monitoring and/or feedback control of the therapy, telemetry circuitry and power. The neuromodulation output circuit 315 produces and delivers neuromodulation pulses. The neuromodulation control circuit 316 controls the delivery of the neuromodulation pulses using the plurality of neuromodulation parameters. The combination of the neuromodulation output circuit 315 and neuromodulation control circuit 316 may collectively be referred to as a pulse generator. The lead system 317 includes one or more leads each configured to be electrically connected to neuromodulation device 312 and a plurality of electrodes 311-1 to 311-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between neuromodulation output circuit 315 and tissue of the patient. The neuromodulation pulses are each delivered from the neuromodulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes. Some embodiments may use a lead system that includes one or more leads of the same or different types such as percutaneous leads, linear paddles, multiple-column paddles, or directional leads, among others.

The neuromodulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. An electrical waveform may be controlled or varied for delivery using electrode configuration(s). The electrical waveforms may be analog or digital signals. In some embodiments, the electrical waveform includes pulses. The pulses may be delivered in a regular, repeating pattern, or may be delivered using complex patterns of pulses that appear to be irregular. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of neuromodulation parameter sets may be available for programming into the neuromodulation system. Furthermore, for example SCS systems may have 32 electrodes (plus an additional electrode of the "can" or enclosure of the device) which exponentially increases the number of neuromodulation parameters sets available for programming. To facilitate such selection, the clinician generally programs the neuromodulation parameters sets through a computerized programming system to allow the optimum neuromodulation parameters to be determined based on patient feedback or other means and to subsequently program the desired neuromodulation parameter sets.

Patient paresthesia perception may be used to program SCS therapy, such as by selecting or determining an appropriate neuromodulation parameter set. The paresthesia induced by neuromodulation and perceived by the patient may be located in approximately the same places of the patient body where pain is sensed and thus the target site of treatment. Conventionally, when leads are implanted within the patient, an operating room (OR) mapping procedure may be performed to apply neuromodulation to test placement of the leads and/or electrodes, thereby assuring that the leads and/or electrodes are implanted in effective locations within the patient.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array. According to various embodiments discussed in this document, in addition to the information of dermatomal coverage such as correspondence between body sites of pain and body sites of induced paresthesia, one or more of patient information such as feedback on the induced paresthesia or patient perception thresholds may be used to optimize the target neuromodulation field. This may not only improve the neuromodulation precision and thus better therapeutic outcome, but may also save a system operator's time and ease the burden of programming a neuromodulation system.

Figure 4:
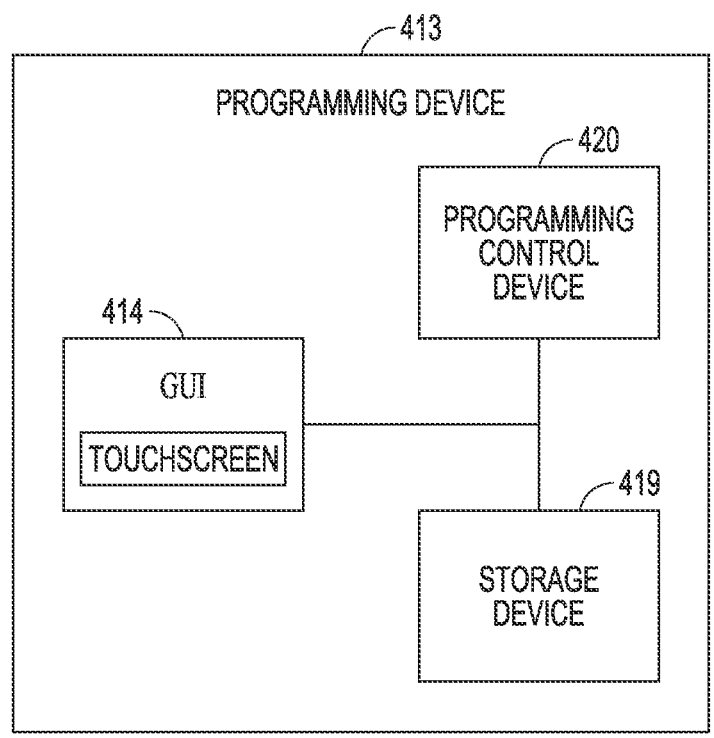
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 419, a programming control circuit 420, and a GUI 414. The programming control circuit 420 generates the plurality of modulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the modulation parameters, such as touchscreen, keyboard, keypad, touchpad, trackball, joystick, and mouse. The storage device 419 may store, among other things, modulation parameters to be programmed into the modulation device. The modulation parameters may be organized into one or more sets of modulation parameters. The programming device 413 may transmit the plurality of modulation parameters to the modulation device. In some embodiments, the programming device 413 may transmit power to the modulation device. The programming control circuit 420 may generate the plurality of modulation parameters. In various embodiments, the programming control circuit 420 may check values of the plurality of modulation parameters against safety rules to limit these values within constraints of the safety rules.

In various embodiments, circuits of neuromodulation, including its various embodiments discussed in this document, may be implemented using a combination of hardware, software and firmware. For example, the circuit of GUI, modulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
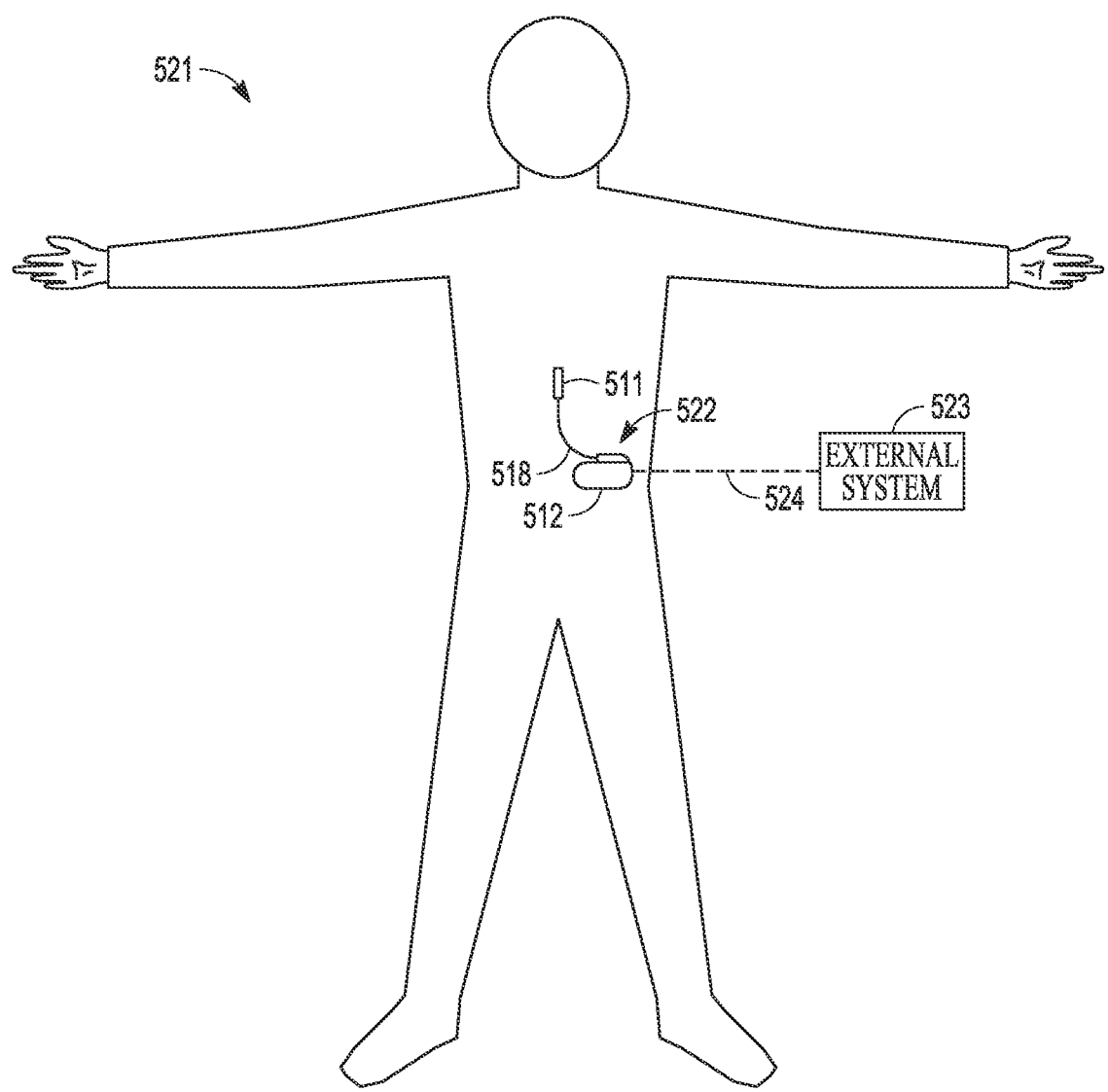
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. The system 521 includes an implantable system 522, an external system 523, and a telemetry link 524 providing for wireless communication between implantable system 522 and external system 523. The implantable system is illustrated as being implanted in the patient's body. The implantable system 522 includes an implantable modulation device (also referred to as an implantable pulse generator, or IPG) 512, a lead system 518, and electrodes 511. The lead system 518 includes one or more leads each configured to be electrically connected to the modulation device 512 and a plurality of electrodes 511 distributed in the one or more leads. In various embodiments, the external system 523 includes one or more external (non-implantable) devices each allowing a user (e.g. a clinician or other caregiver and/or the patient) to communicate with the implantable system 522. In some embodiments, the external system 523 includes a programming device intended for a clinician or other caregiver to initialize and adjust settings for the implantable system 522 and a remote control device intended for use by the patient. For example, the remote control device may allow the patient to turn a therapy on and off and/or adjust certain patient-programmable parameters of the plurality of modulation parameters. The external system 523 may include other local or remote servers or computer systems accessible through a variety of network(s).

The neuromodulation lead(s) of the lead system 518 may be placed proximate to (e.g. such as resting near, or upon the dura, adjacent to) the dorsal root tissue to be stimulated. Due to the lack of space near the location of the implanted neuromodulation lead(s), the implantable modulation device 512 may be implanted in a surgically-made pocket either in the abdomen or above the buttocks, or may be implanted in other locations of the patient's body. The lead extension(s) may be used to facilitate the implantation of the implantable modulation device 512 away from the exit point of the neuromodulation lead(s).

Figure 6:
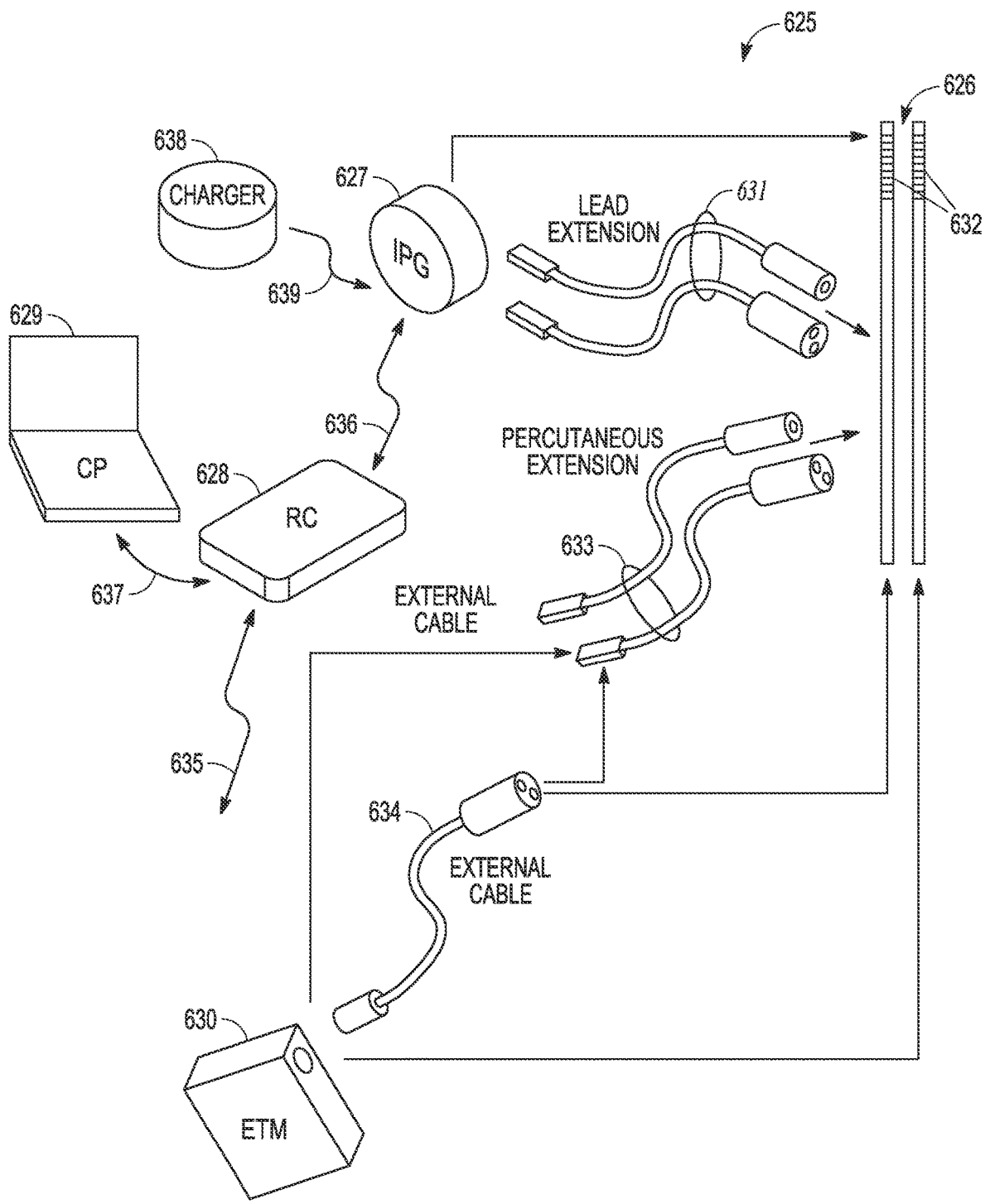
FIG. 6 illustrates, by way of example, an embodiment of a Spinal Cord Stimulation (SCS) system, which also may be referred to as a Spinal Cord Modulation (SCM) system.

FIG. 6 illustrates, by way of example, an embodiment of a SCS system, which also may be referred to as a Spinal Cord Modulation (SCM) system. The SCS system 625 may generally include a one or more (illustrated as two) of implantable neuromodulation leads 626, an implantable pulse generator (IPG) 627, an external remote controller RC 628, a clinician's programmer (CP) 629, and an external trial modulator (ETM) 630. The IPG 627 may be physically connected via one or more percutaneous lead extensions 631 to the neuromodulation lead(s) 626, which carry a plurality of electrodes 632. The electrodes, when implanted in a patient, form an electrode arrangement. As illustrated, the neuromodulation leads 626 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 627 includes pulse generation circuitry that delivers electrical modulation energy in the form of a pulsed electrical waveform (i.e., a temporal series of electrical pulses) to the electrodes in accordance with a set of modulation parameters.

The ETM 630 may also be physically connected via the percutaneous lead extensions 633 and external cable 634 to the neuromodulation lead(s) 626. The ETM 630 may have similar pulse generation circuitry as the IPG 627 to deliver electrical modulation energy to the electrodes accordance with a set of modulation parameters. The ETM 630 is a non-implantable device that may be used on a trial basis after the neuromodulation leads 626 have been implanted and prior to implantation of the IPG 627, to test the responsiveness of the modulation that is to be provided. Functions described herein with respect to the IPG 627 can likewise be performed with respect to the ETM 630.

The RC 628 may be used to telemetrically control the ETM 630 via a bi-directional RF communications link 635. The RC 628 may be used to telemetrically control the IPG 627 via a bi-directional RF communications link 636. Such control allows the IPG 627 to be turned on or off and to be programmed with different modulation parameter sets. The IPG 627 may also be operated to modify the programmed modulation parameters to actively control the characteristics of the electrical modulation energy output by the IPG 627. A clinician may use the CP 629 to program modulation parameters into the IPG 627 and ETM 630 in the operating room and in follow-up sessions.

The CP 629 may indirectly communicate with the IPG 627 or ETM 630, through the RC 628, via an IR communications link 637 or other link. The CP 629 may directly communicate with the IPG 627 or ETM 630 via an RF communications link or other link (not shown). The clinician detailed modulation parameters provided by the CP 629 may also be used to program the RC 628, so that the modulation parameters can be subsequently modified by operation of the RC 628 in a stand-alone mode (i.e., without the assistance of the CP 629). Various devices may function as the CP 629. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 629. Alternatively, such programming methodologies can be performed using firmware or hardware. In any event, the CP 629 may actively control the characteristics of the electrical modulation generated by the IPG 627 to allow the desired parameters to be determined based on patient feedback or other feedback and for subsequently programming the IPG 627 with the desired modulation parameters. To allow the user to perform these functions, the CP 629 may include user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads, and select and program the IPG with modulation parameters, including electrode selection, in both a surgical setting and a clinical setting. The display screen(s) may be used to suggest the electrode(s) for use to stimulate a targeted dorsal root. The external device(s) (e.g. CP and/or RC) may be configured to communicate with other device(s), including local device(s) and/or remote device(s). For example, wired and/or wireless communication may be used to communicate between or among the devices.

An external charger 638 may be a portable device used to transcutaneously charge the IPG via a wireless link such as an inductive link 636. Once the IPG has been programmed, and its power source has been charged by the external charger or otherwise replenished, the IPG may function as programmed without the RC or CP being present.

Figure 7:
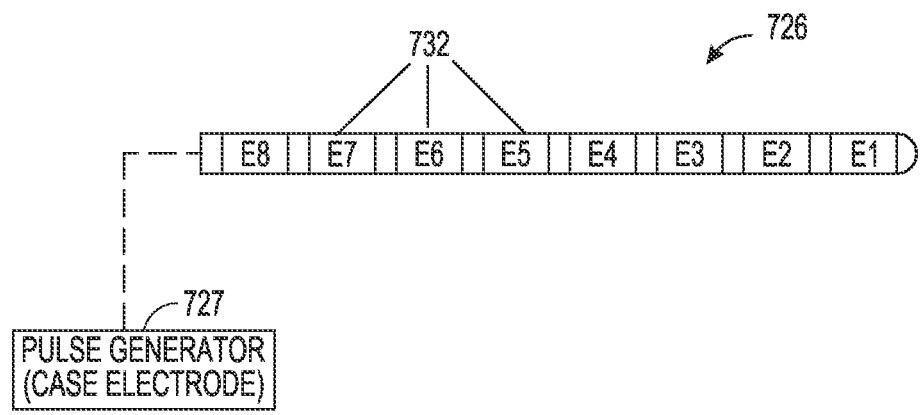
FIG. 7 illustrates, by way of example, some features of the neuromodulation lead and a waveform generator.

FIG. 7 illustrates, by way of example, some features of the neuromodulation leads 726 and a pulse generator 727. The pulse generator 727 may be an implantable device (IPG) or may be an external device such as may be used to test the electrodes during an implantation procedure. In the illustrated example, the neuromodulation lead has eight electrodes 732 (labeled E1-E8). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, modulation output circuitry, and other suitable components known to those skilled in the art. The microcontroller executes a suitable program stored in memory, for directing and controlling the neuromodulation performed by IPG. Electrical modulation energy is provided to the electrodes in accordance with a set of modulation parameters programmed into the pulse generator. The electrical modulation energy may be in the form of a pulsed electrical waveform. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (which may be measured in milliamps or volts depending on whether the pulse generator supplies constant current or constant voltage to the electrode array), pulse width (which may be measured in microseconds), pulse rate (which may be measured in pulses per second), and burst rate (which may be measured as the modulation on duration X and modulation off duration Y). Electrodes that are selected to transmit or receive electrical energy are referred to herein as "activated," while electrodes that are not selected to transmit or receive electrical energy are referred to herein as "non-activated."

Electrical modulation occurs between or among a plurality of activated electrodes, one of which may be the IPG case. The system may be capable of transmitting modulation energy to the tissue in a monopolar or multipolar (e.g., bipolar, tripolar, etc.) fashion. Monopolar modulation occurs when a selected one of the lead electrodes is activated along with the case of the IPG, so that modulation energy is transmitted between the selected electrode and case. Any of the electrodes E1-E8 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical modulation energy that is therapeutically effective and causes the patient to perceive delivery of the energy (e.g. therapeutically effective to relieve pain with perceived paresthesia), and may be operated in a sub-perception mode to deliver electrical modulation energy that is therapeutically effective and does not cause the patient to perceive delivery of the energy (e.g. therapeutically effective to relieve pain without perceived paresthesia).

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control of the shape and size of the resulting modulation field, a single output source switched across electrodes may also be used, although with less fine control in programming. Neuromodulators may be designed with mixed current and voltage regulated devices.

Figure 8:
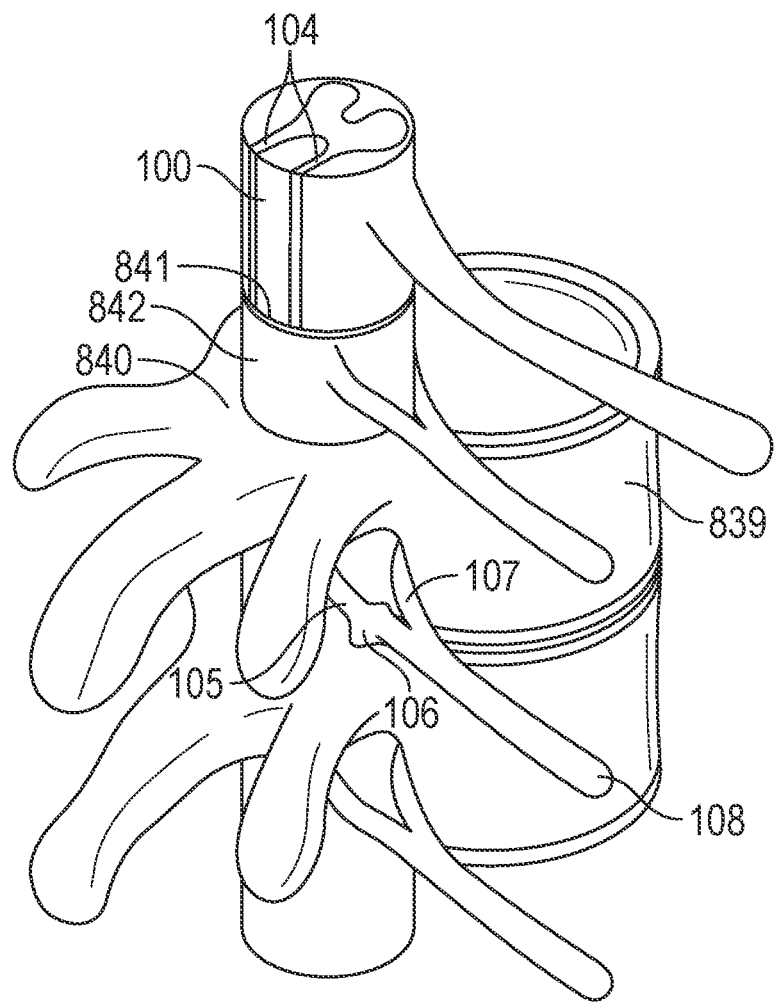
FIG. 8 illustrates a partial view of both neuroanatomy and bony anatomy of the spinal column.

FIG. 8 illustrates, for the convenience of the reader, a partial view of both neuroanatomy and bony anatomy of the spinal column. The neuroanatomy includes the spinal cord 100 such as was illustrated in FIG. 1. The neuroanatomy also includes the dorsal horn (DH) 104, the dorsal root 105, the DRG 106, the ventral root 107, and the mixed spinal nerve root 108. The bony anatomy refers to the vertebrae that includes a vertebral body 839 and a bony ring 840 attached to the vertebral body 839. The stacked vertebrae provide a vertebral canal that protects the spinal cord 100. Nerve roots branch off and exit the spine on both sides through spaces ('intervertebral foramen") between the vertebra. The spinal cord is surrounded by dura matter 841, which holds spinal fluid that surrounds the spinal cord 100. The space between the walls and the dura matter of the vertebral canal is referred to as epidural space 842.

FIGS. 9A-9C illustrate a transverse top view, a coronal side view and an angled view, respectively, of the spinal cord 100, the dorsal root 105, the DRG 106, the ventral root 107 and the mixed spinal nerve root 108. FIG. 9A also illustrates bone 943, fat 944, dura 945 and cerebrospinal fluid 946.

Figure 10B:
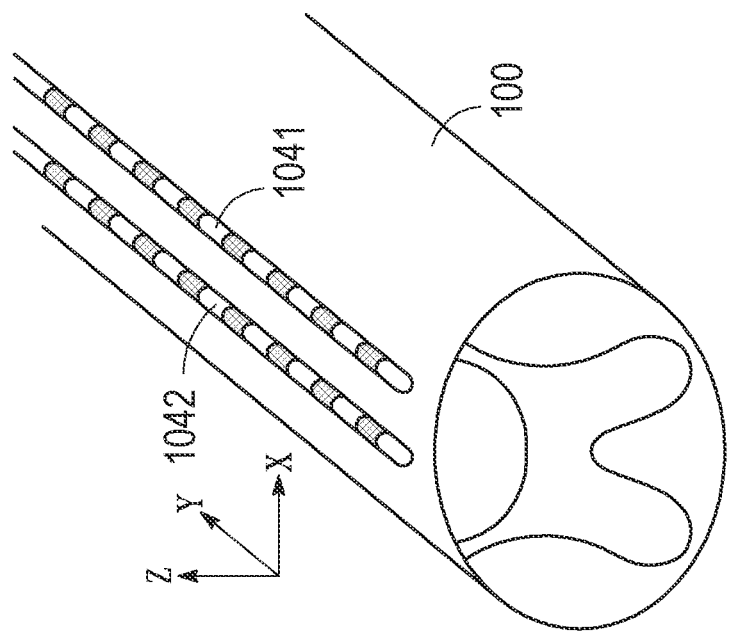
FIGS. 10A-10G illustrate, by way of example, various examples of lead placement on a spinal cord.
Figure 10A:
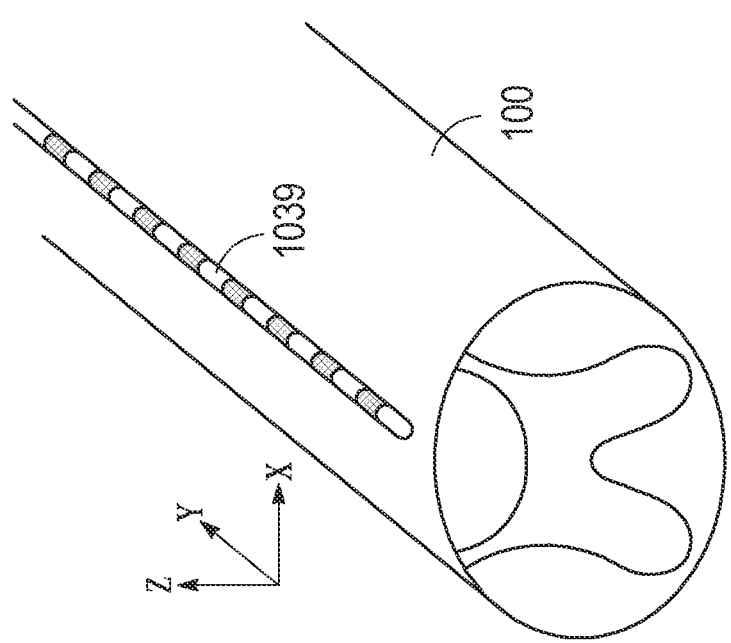

FIGS. 10A-10G are schematic views of embodiments of neuromodulation lead placement on a patient's spinal cord. Specifically, FIG. 10A is a schematic view of a single electrical neuromodulation lead 1039 implanted over approximately the longitudinal midline of the spinal cord 100. It is understood that additional leads or lead paddle(s) may be used, such as may be used to provide a wider electrode arrangement and/or to provide the electrodes closer to dorsal horn elements, and that these electrode arrays also may implement fractionalized current. FIG. 10B illustrates an embodiment where two electrical neuromodulation leads are implanted near the spinal cord. A first electrical neuromodulation lead 1041 is implanted more laterally with respect to the spinal cord, thereby placing it proximate the dorsal horn of the spinal cord. A second electrical neuromodulation lead 1042 is implanted more medially with respect to the spinal cord, thereby placing it proximate the dorsal column of the spinal cord 100.

Placement of the lead more proximal to the DH than the DC may be desirable to preferentially stimulate DH elements over DC neural elements for a sub-perception therapy. Lead placement may also enable preferential neuromodulation of dorsal roots over other neural elements. Any other plurality of leads or a multiple column paddle lead can also be used. Longitudinal component of the electrical field is directed along the y-axis depicted in each of FIGS. 10A-10B, and a transverse component of the electrical field is directed along the x-axis depicted in each of FIGS. 10A-10B. Some embodiments may include directional leads with one or more directional electrodes. A directional electrode may extend less than 360 degrees about the circumference of a lead body. For example, a row of two or more directional electrodes (e.g. "segmented electrodes") may be positioned along the circumference of the lead body. Activating select ones of the segmented electrodes may help extend and shape the field in a preferred direction.

Figure 10C:
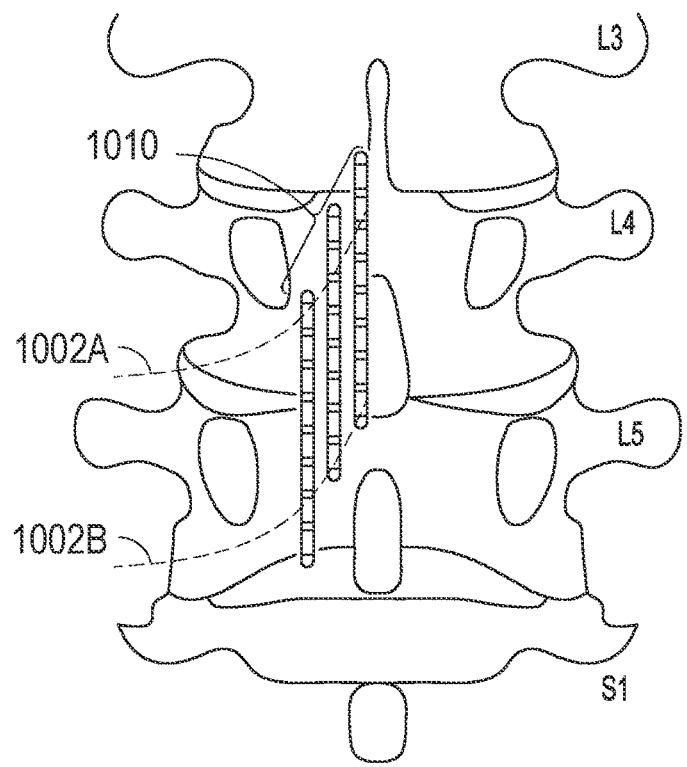
Figure 10D:
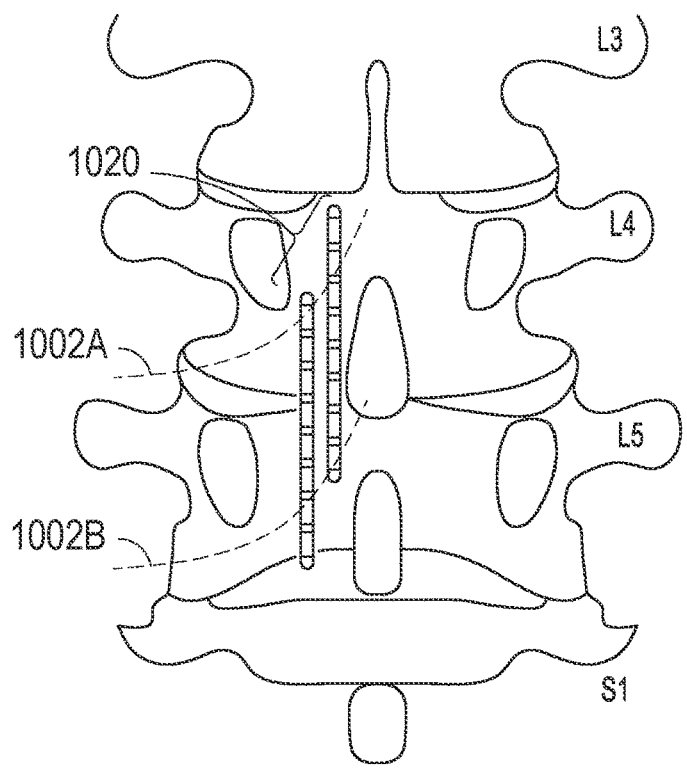
Figure 10F:
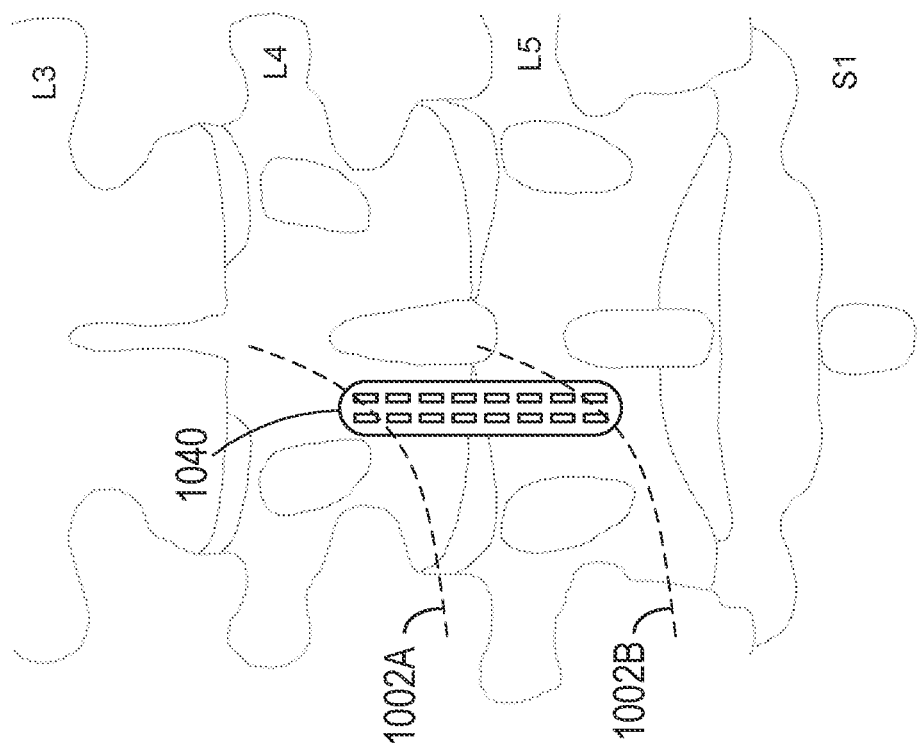
Figure 10E:
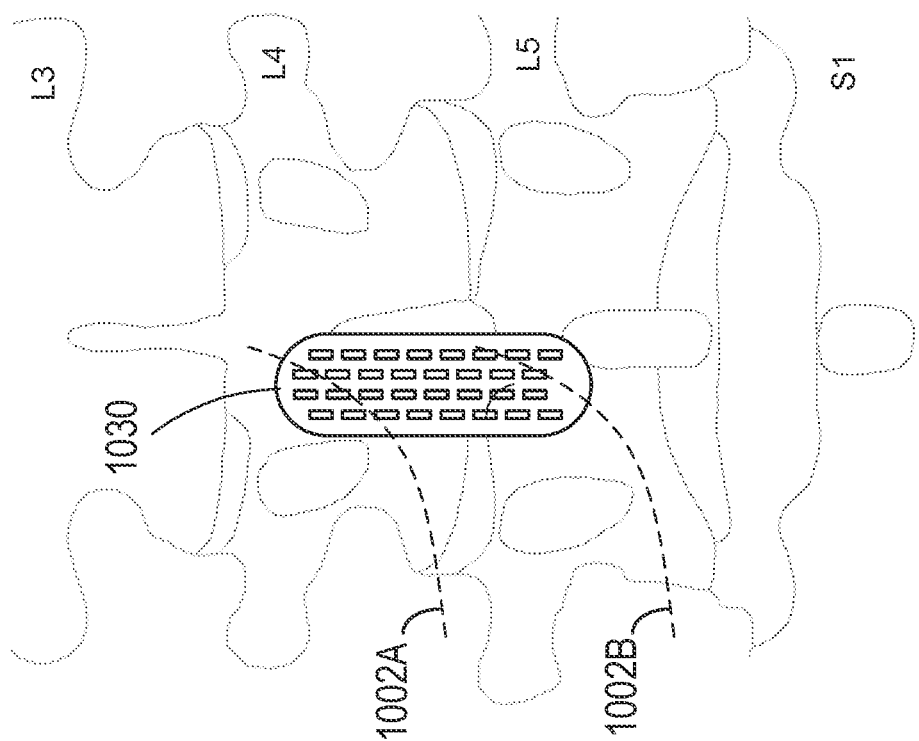
Figure 10G:
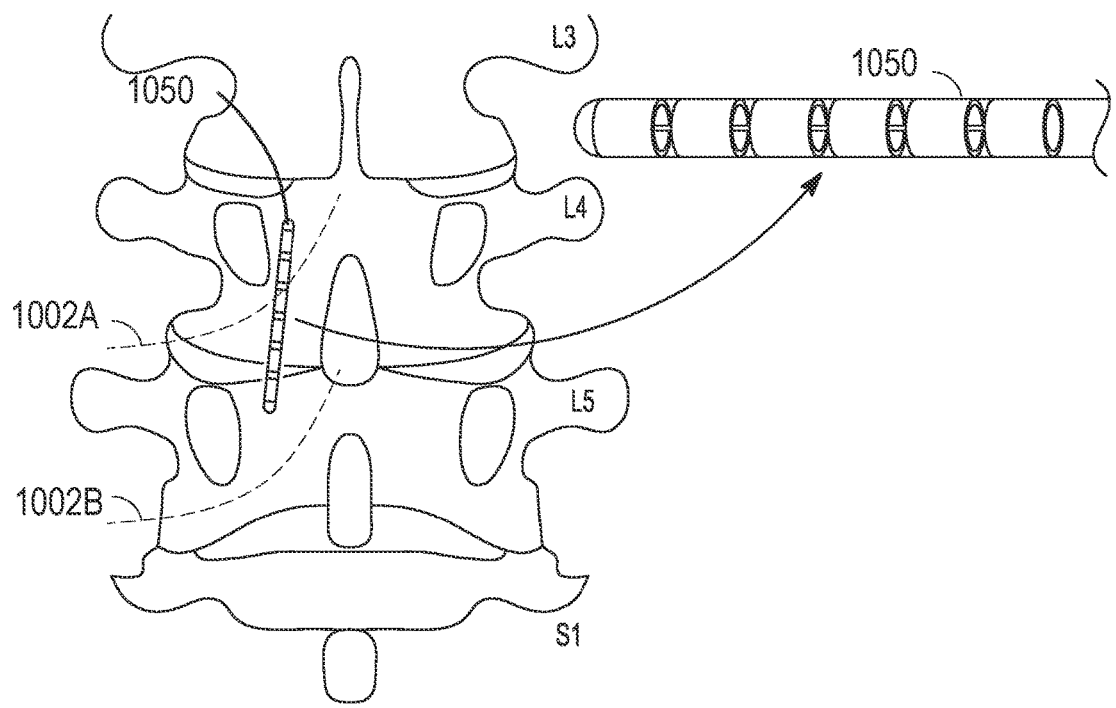

It is to be understood that additional neuromodulation leads or paddle(s) of the same or different types may be used, such as may be used to provide a wider electrode arrangement and/or to provide the electrodes closer to dorsal horn elements. In some examples, the neuromodulation leads or paddles may be placed at regions more caudal to the end of the spinal cord, and the electrode arrays on the neuromodulation lead also may implement fractionalized current. FIGS. 10C-10G are schematic views of embodiments of neuromodulation lead placement on caudal regions of spinal column, such as the level of L3-L5 and S1, where virtually no spinal cord, but only dorsal roots, among other neural structures, are present. The neuromodulation leads or paddles may be placed medial or lateral to the spinal column, and proximal to one or more dorsal roots, and are configured to deliver modulation energy to the dorsal root fibers. In FIG. 10C, three percutaneous leads 1010 are positioned toward the left side of the spinal canal, and in FIG. 10D two percutaneous leads 1020 are positioned toward the left side of the spinal canal. In FIG. 10E, a single four-column paddle lead 1030 is positioned toward the left side of the spinal canal, and in FIG. 10F, a single two-column paddle lead 1040 is positioned toward the left side of the spinal canal. In FIG. 10G, a single percutaneous lead 1050 is positioned toward the left side of the spinal canal. In the illustrated example, the percutaneous lead 1050 includes multiple segmented electrodes that enable lateral control of the stimulation location via a single lead. Moreover, because the segmented electrodes are placed in close lateral proximity, they can be used to provide a high degree of lateral stimulation resolution.

While the examples illustrated in FIGS. 10C-10G show electrode lead placements to the left side of the spinal canal, these are by way of example and not limitation. In any of FIGS. 10C-10G, lead placements to the right side of the spinal canal may also be utilized. As can be seen from the figures, different types of leads with different numbers of electrodes and different electrode spacing (including different types than those shown) may be employed to provide dorsal root stimulation. These example lead placements differ from the placement of leads more proximal to the anatomical midline in traditional spinal cord stimulation (SCS) therapy.

The dorsal root trajectories 1002A and 1002B in FIGS. 10C-10G show that dorsal root fibers have different trajectories from dorsal column fibers, and they are not aligned with the anatomical midline. Accordingly, relative locations (e.g., lead entry angles) between the lead and the neural targets (e.g., dorsal column fibers or dorsal root fibers) can vary at different anatomical regions, as shown in FIGS. 10C-10G. When neuromodulation is specifically being targeted to dorsal root fibers, it is desirable to know the locations of the dorsal roots such that stimulation can be customized. The present document describes various embodiments of incorporating anatomy information of target neural tissue (e.g., trajectory of dorsal roots) and patient feedback to paresthesia into the process of stimulation field design, which may help improve the neuromodulation precision and thus better therapeutic outcome such as pain relief.

Figure 10H:
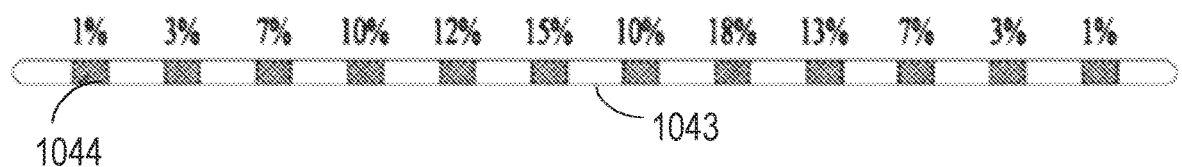
FIG. 10H illustrates, by way of example, fractionalization of anodic current delivered to the electrodes on an electrical neuromodulation lead.

FIG. 10H is a schematic view of an electrical neuromodulation lead 1043 showing an example of the fractionalization of the anodic current delivered to the electrodes on the electrical neuromodulation lead. These figures illustrate fractionalization using monopolar neuromodulation where a case electrode of the IPG is the only cathode, and carries 100% of the cathodic current. The fractionalization of the anodic current shown in FIG. 10E does not deliver an equal amount of current to each electrode 1044, because this embodiment takes into account electrode/tissue coupling differences, which are the differences in how the tissue underlying each electrode reacts to electrical neuromodulation. Also, the ends of the portion of the electrical neuromodulation lead include electrodes having lower gradient in the longitudinal direction. The magnitude of the electrical field tapers down at the ends of the electrical neuromodulation lead. Fractionalization of the current may accommodate variation in the tissue underlying those electrodes. The fractionalization across the electrical neuromodulation lead can vary in any manner as long as the total of fractionalized currents equals 100%. Various embodiments described herein implement a programmed algorithm to determine the appropriate fractionalization to achieve a desired neuromodulation field property.

Neuromodulation thresholds vary from patient to patient and from electrode to electrode within a patient. An electrode/tissue coupling calibration of the electrodes may be performed to account for these different neuromodulation thresholds and provide a more accurate fractionalization of the current between electrodes. For example, perception threshold or neural threshold also known as Evoked Compound Action Potential (ECAP) threshold may be used to normalize the electrodes. In this case, the ECAP threshold considered can be the dorsal root threshold, and the system may have physiological sensing capabilities and signal processing capabilities to analyze the signals recorded, and determine the smallest amplitude that triggers the presence of an ECAP. The smallest amplitude thus determined may represent the neural or ECAP threshold. The RC or the CP may be configured to prompt the patient to actuate a control element, once paresthesia is perceived by the patient. In response to this user input, the RC or the CP may be configured to respond to the user input by storing the neuromodulation signal strength when the control element is actuated. Other sensed parameter or patient-perceived neuromodulation values (e.g. constant paresthesia, or maximum tolerable paresthesia) may be used to provide the electrode/tissue coupling calibration of the electrodes.

The SCS system may be configured to deliver different electrical fields to achieve a temporal summation of neuromodulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a neuromodulation parameter set to create a stimulation field definition to reduce or minimize neuromodulation of non-targeted tissue (e.g. DC tissue). The neuromodulation field may be shaped by using multiple independent current control (MICC) or multiple independent voltage control to guide the estimate of current fractionalization among multiple electrodes and estimate a total amplitude that provide a desired strength. For example, the neuromodulation field may be shaped to enhance the neuromodulation of DH neural tissue and to minimize the neuromodulation of DC tissue. A benefit of MICC is that MICC accounts for various in electrode-tissue coupling efficiency and perception threshold at each individual contact, so that "hot-spot" stimulation is eliminated.

FIGS. 11A-11B illustrate, by way of example and not limitation, schematic views of embodiments of neuromodulation lead placement on a patient's spinal cord. FIG. 11A illustrates an epidural mid-line lead 1110 that targets the dorsal column 103. The mid-line epidural lead 1110 may or may not provide the desired coverage of the focal pain area, and may or may not provide stimulation spill over. Furthermore, it can be challenging to find settings to cover both low back and focal pain. FIG. 11B illustrates an epidural lateral lead 1120 which, in accordance with various examples as discussed herein, can provide more effective stimulation targeting lateral spinal neural targets, such as the dorsal root 105, the dorsal rootlets 109, or the DREZ 119.

Figure 12A:
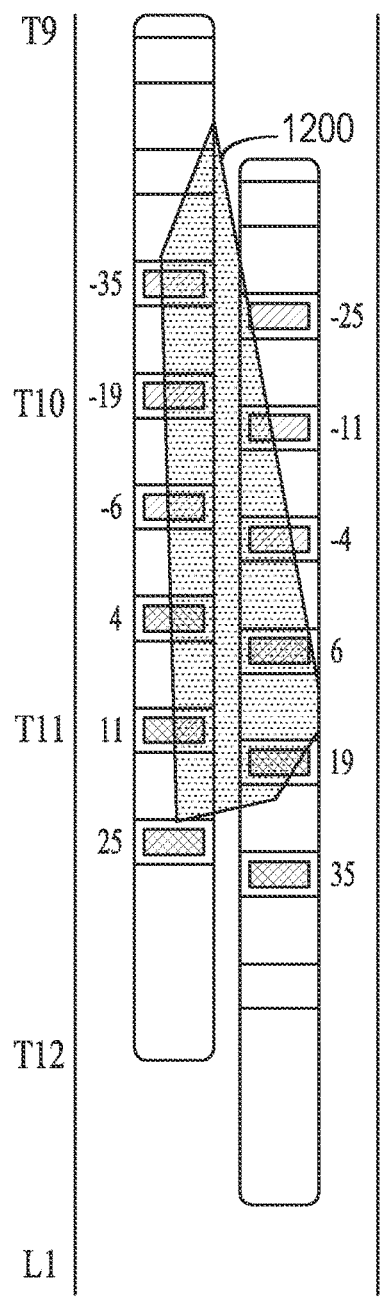
FIGS. 12A and 12B illustrate, by way of example, anatomical regions on a patient body where pain is felt (pain sites).
Figure 12B:
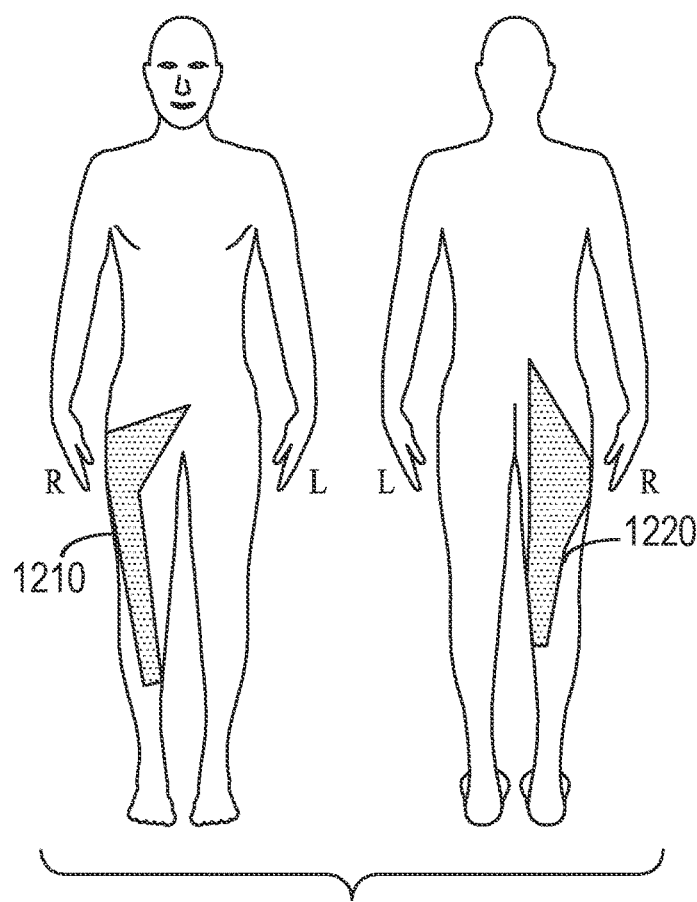

One aspect of the embodiments discussed in this document is directed to automatic identification of lateral spinal neural targets corresponding to the epidural leads placement and focal pain areas, and generating a selectable set of therapy options such as electrode configurations for neurostimulation. The focal pain areas may be identified by the patient using a pain map. FIGS. 12A and 12B are diagrams illustrating, by way of example and not limitation, anatomical regions on a patient body where pain is felt (pain sites), or anatomical region on a patient body where the effect of neurostimulation delivery, such as paresthesia, is perceived (paresthesia sites). The anatomical sites may be drawn (e.g., free-hand drawing by the patient), derived from a patient pain drawing or paresthesia drawing via a look up table or an algorithm, or using a combination of the methods thereof. FIG. 12A illustrates an example of a drawing 1200 of target sites over a representation of a plurality of electrodes implanted in a patient. The target sites may be pain sites (in which case the drawings 1200, 1210, and 1220 are referred to as pain drawings), or paresthesia sites (in which case the drawings 1200, 1210, and 1220 are referred to as paresthesia drawings). FIG. 12B illustrates, by way of example and not limitation, drawings representing pain sites or paresthesia sites on an illustrative diagram of a human body including one or both of ventral and dorsal depiction of the body. In the illustrated example, pain sites or the paresthesia sites are marked in a first drawing 1210 on a ventral depiction of the body, and in a second drawing 1220 on a dorsal depiction of the body. The pain drawing and the paresthesia drawing may be respectively generated, and provided to a neuromodulation control system. In an example, the pain sites or the paresthesia sites may be mapped to specific dermatome compartments on the skin. The mapping may be a point-by-point mapping via a look-up table or a dictionary/key system. The center, length, and width of the target linear field may be determined based on the spatial extent of the spinal cord region corresponding to the patient's reported pain region. A clinician or other specialist, a patient or a combination of persons may work together to highlight region of spinal cord and/or body where they want stimulation to be targeted (i.e. focus stimulation on anatomical correlate and/or reported site of pain). Internal look-up table and/or inverse algorithm with field "primitives" tied to specific regions/region sizes may be used to display and configure electrode settings according to this anatomically-based specification.

Figure 13:
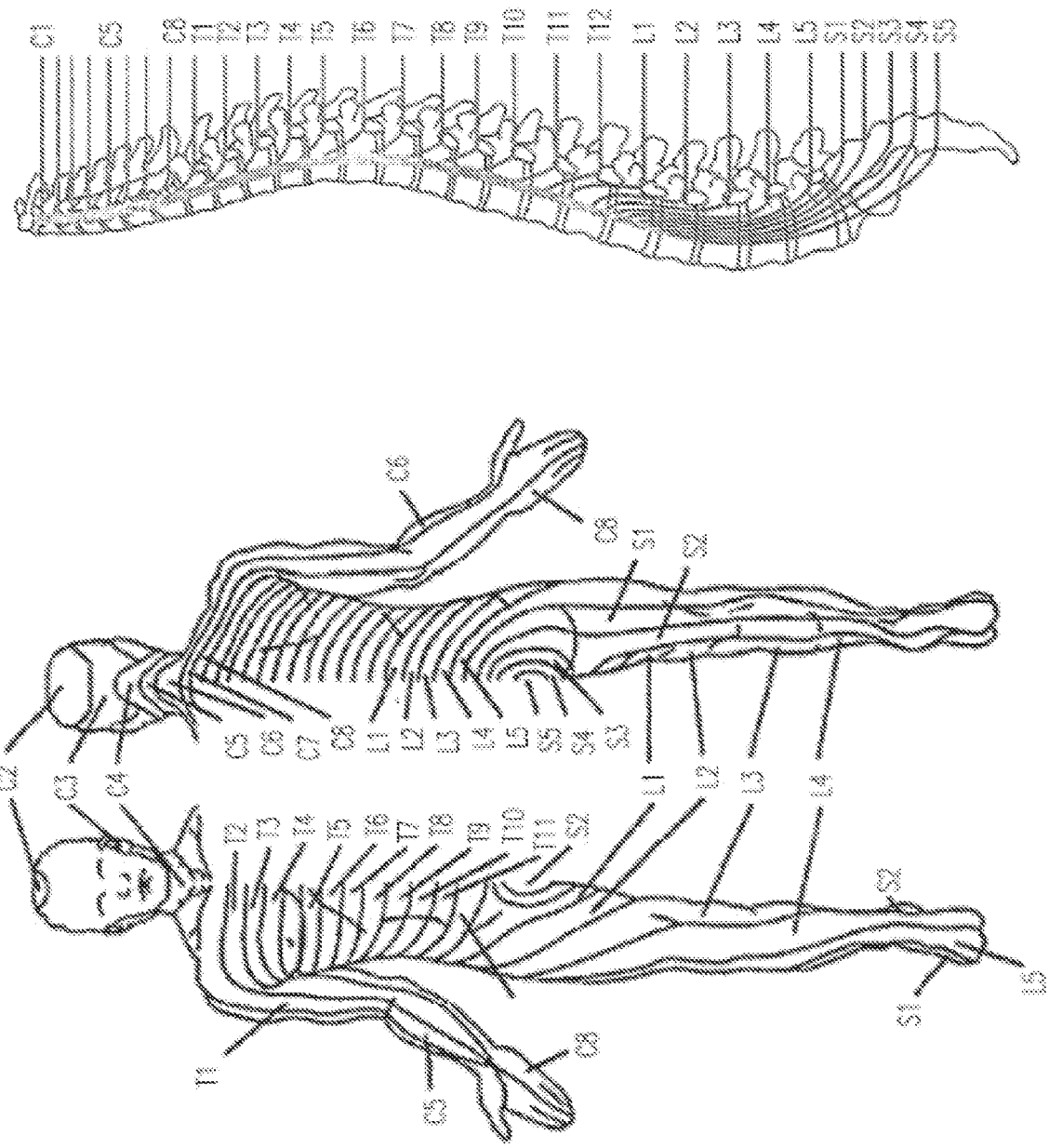
FIG. 13 illustrates generally an example of dermatomes in a human body and the corresponding spinal nerves coming from the spinal cord.

FIG. 13 illustrates generally an example of dermatomes in a human body and the corresponding spinal nerves coming from the spinal cord. Originating from the spinal cord there are eight cervical nerves (C1 through C8), twelve thoracic nerves (T1 through T12), five lumbar nerves (L1 through L5), and five sacral nerves (S1 through S5). Each of these nerves relays sensations, including pain, from a particular region of skin to the brain. Successful pain management and the avoidance of stimulation in unafflicted regions require the applied electric field to be properly positioned longitudinally along the spinal cord and nearby structures.

A dermatome is an area of skin that is supplied by sensory neurons that arise from a spinal nerve ganglion at a given spinal cord level. Except for the cervical nerve C1, which maps to no dermatome, a total of 29 spinal nerves (including cervical nerves C2-C8, thoracic nerves T1-T12, lumbar nerves L1-L5, and sacral nerves S1-S5) can be mapped to a respective dermatome, resulting in 29 dermatomes distributed across the body surface. In particular, the head and neck regions are associated with C2-C8, the back is associated with C2-S3, the central diaphragm is associated with C3-C5, the upper extremities are associated with C5-T1, the thoracic wall is associated with T1-T11, the peripheral diaphragm is associated with T6-T11, the abdominal wall is associated with T6-L1, lower extremities are located from L2-S2, and the perineum from L4-S4. For example, chronic pain sensations commonly focus on the lower back and lower extremities, which correspond to T8-T10. A specific energy field can be applied to the corresponding spinal nerves to treat the chronic pain in the area.

Figure 14:
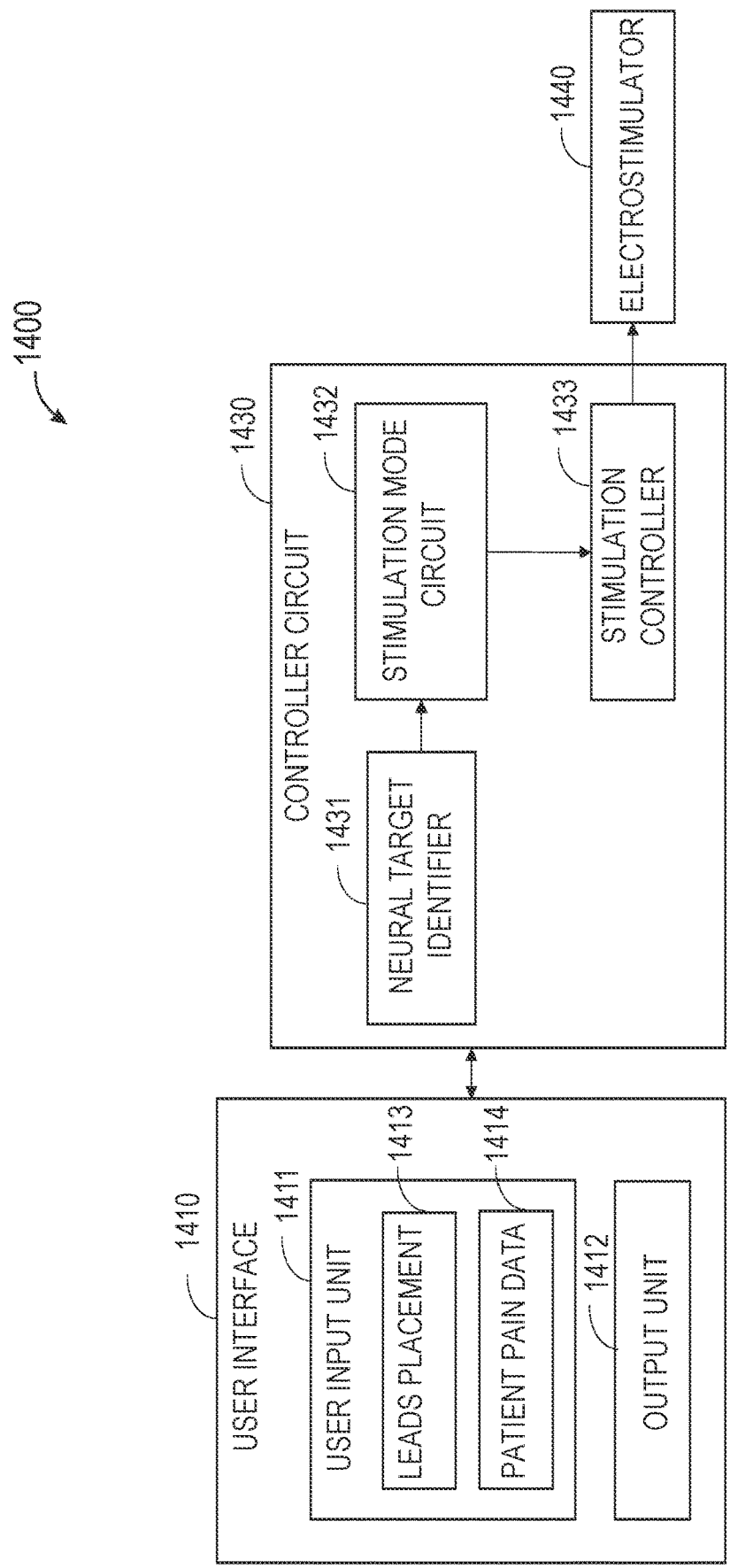
FIG. 14 is a block diagram illustrating, by way of example, a neuromodulation system that provides selectable lateral SCS for pain control.

FIG. 14 is a block diagram illustrating, by way of example and not limitation, a neuromodulation system 1400 configured to provide selectable lateral spinal cord stimulation (SCS) for pain control. The neuromodulation system 1400, which is an embodiment of the neuromodulation system 210, may include one or more of a user interface 1410, a controller circuit 1430, and electrostimulator 1440. Portions of the neuromodulation system 1400 may be implemented in the implantable system 521 or the external system 522. In an example, the user interface 1410 and the controller circuit 1430 may be included in a programming device, such as the programing device 413.

The user interface 1410, which is an example of the GUI 414, includes a user input unit 1411 and an output unit 1412. The user input unit 1411 may include one or more user interface (UI) controls that may be used by the user to provide information about leads placement 1413. The leads placement 1413 may include a selection from a plurality of lead types including, for example, percutaneous cylindrical leads, linear paddles, multiple-column paddles, or directional leads with segmented electrodes (hereinafter cumulatively referred to as "leads"), and placement of the selected one or more leads at respective locations on a graphical spinal cord representation displayed on the user interface 1410, as shown in FIGS. 10A-10F and 11A-11B. Examples of placing one or more leads on a graphical spinal cord representation are described below with reference to FIGS. 15A and 16A.

The user input unit 1411 may receive patient pain data 1414. The patient pain data 1414 may include indications of anatomical locations of the pain perceived by the patient (pain sites). The patient pain data 1414 may additionally include one or more of distribution of the pain, intensity of pain at various pain sites, or temporal pattern such as persistence of the pain at various pain sites, among other pain information. The patient pain data 1414 may be represented by texts, graphs, verbal description, among other means of representation. In an example, the patient pain data 1414 includes a pain drawing, such as that illustrated in FIGS. 12A-12B. The pain drawing may include pain markings, provided by the patient, that identify the locations where pain radiates or expands. The pain markings may additionally include different symbols to distinguish various pain sensations, such as aching, numbness, burning, stabbing, or needle pain. Additionally or alternatively, the pain markings may include different symbols to distinguish various intensities of the pain at each marked pain location. In some examples, the patient pain data 1414 may include a patient questionnaire or patient pain description. In some examples, the patient pain data 1414 may include reference data, such as a dermatome map that identifies (e.g., using labels, markers, or annotations) various skin areas corresponding to spinal nerves that innervates said skin areas, such as that illustrated in FIG. 13. Such pain-associated dermatomes are referred to as pain dermatomes, and can be automatically identified. Examples of the patient pain data 1414 such as a patient pain drawing and pain dermatomes are described below with reference to FIG. 15A.

The controller circuit 1430, which is an example of the programming control circuit 420, can determine an optimal pain therapy including electrode configuration for delivering neurostimulation. The controller circuit 1430 may include circuit sets comprising one or more other circuits or sub-circuits, such as a neural target identifier 1431, a stimulation mode circuit 1432, and a stimulation controller 1433. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the controller circuit 1430 may be implemented as a part of a microprocessor circuit. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the functions, methods, or techniques described herein.

The neural target identifier 1431 may identify one or more neural targets based at least on the information about leads placement 1413. By way of example and not limitation, for a lead placed in a vicinity of a lateral portion of certain spinal cord level(s) (such as the epidural lateral lead 1120 on the graphical spinal cord representation as shown in FIG. 11B), the neural target identifier 1431 may identify the corresponding lateral spinal neural targets such as the dorsal root 105, the dorsal rootlets 109, or the DREZ 119 at the spinal cord levels where the lead is placed. In some examples, the leads placement 1413 may include placement of multiple leads at respective portions (e.g., lateral portions) of the graphical spinal cord representation. Each lead comprises an array of electrodes interfacing with the spinal cord at respective electrode-tissue contacts. The neural target identifier 1431 may generate one or more contact groups. Each contact group comprises a plurality of electrode-tissue contacts associated with electrodes on the same lead or electrodes on two or more different leads. The contact groups may be at different locations of the spinal cord. For a contact group, the neural target identifier 1431 may identify corresponding spinal neural targets based on locations of the electrode-tissue contacts of that contact group. In an example as illustrated in FIG. 15B, a first contact group may correspond to first lateral spinal neural targets including dorsal column, dorsal rootlets, DREZ, a Lissauer's track, and inhibitory interneurons; a second contact group may correspond to second lateral spinal neural targets including one or more midline dorsal roots; and a third contact group may correspond to third lateral spinal neural targets including one or more lateral dorsal roots.

The neural target identifier 1431 may identify one or more neural targets further based on the patient pain data 1414, such as user input of pain area(s) or the corresponding pain dermatome(s), and detect neural thresholds at each contact or contact group during stimulation mapping. In an example, the neural target identifier 1431 may determine a rostral-caudal position and/or a medio-lateral position of a contact group relative to spinal cord level(s) innervating the dermatomes corresponding to the pain areas (the pain dermatomes), and identify neural targets of interest depending on whether the electrode-tissue contacts of the contact group are at, or being rostral or caudal to, the spinal level of pain dermatomes. Examples of generating different contact groups and identifying respective neural targets for the contact groups, and display the same on a user interface, are described below with reference to FIG. 15B.

In addition to or in lieu of the automatic identification of neural targets based on user input of the leads placement 1413 and optionally the patient pain data 1414, in some examples, a user (e.g. a clinician or other caregiver and/or the patient) may manually identify one or more neural targets, such as by selecting from a list of pre-generated candidate neural targets, via the user input unit 1411 of the user interface 1410. Examples of manual selection of the neural targets on a user interface are discussed below with reference to FIGS. 16B-16D.

The stimulation mode circuit 1432 may generate selectable electrostimulation settings for a spinal neural target, such as a lateral spinal neural target automatically identified by the neural target identifier 1431, or a lateral spinal neural target manually selected by the user. The electrostimulation setting may include a stimulation mode, which indicates electrode configurations (e.g., monopolar, bipoloar, or tripolar stimulation, anode and cathode designation). The electrostimulation setting may include a location of central point of stimulation that represents a focal point of a stimulation field. The electrostimulation setting may additionally or alternatively include one or more stimulation parameters, such as a current amplitude or a voltage amplitude, a pulse width, a pulse shape (waveform), a pulse rate, a duty cycle, any other static parameter, or a modulation waveform continuously adjusting the amplitude, or the pulse width, or the frequency of the trains of pulses, where the modulation waveform can be a random signal, sinewave, triangular, exponential, logarithmic, quadratic, or any other modulating function, and the function parameters become other parameters among the parameters including those listed herein.

The selectable electrostimulation setting may include paresthesia-based stimulation modes, which may cause paresthesia sensation during stimulation. Examples of the paresthesia-based stimulation modes include a monopolar stimulation mode, a bipolar stimulation mode, a tripolar stimulation mode, asteering mode, a Sensations mode, and a rotation mode. The stimulation may be cathodic or anodic. In an example, monopolar anodic stimulation may be applied after a search using MICC through the different electrode-tissue contacts. In an example, monopolar anodic stimulation may be applied with Time-Variant Pulses (TVPs), such as defined as rate, pulse width, or amplitude modulated with a specific function, such as a sinusoidal wave function, a random function following a statistical distribution (e.g., a Poisson distribution, or a uniform distribution), or other arbitrary waveforms. TVPs with monopolar anodic stimulation may be applied after a sweet spot search is done using MICC through the different contacts. A sweet spot is a desirable or optimal location for the neuromodulation field. In an example, a test region may be primed with the sub-perception neuromodulation field, and a sweet-spot can be identified as a neural tissue that is therapeutically effective when targeted with sub-perception neuromodulation. The sweet spot test may involve a manual process to reprogram the neuromodulation field parameter set with different values to change the targeted location of the neuromodulation field. In some embodiments of the test, the targeted location may be automatically changed (e.g. trolled) by automatically changing values of the neuromodulation field parameter set. Some embodiments may semi-automatically change values of the neuromodulation field parameter set to change the targeted location of the neuromodulation field. In an example, monopolar cathodic stimulation may be applied with or without the TVPs. In another example, bipolar stimulation may be applied with or without TVPs. The bipolar configuration comprises an anode located at the rootlets, and a cathode located in the mid-lead. In an example, a tripolar stimulation may be applied in the rostrocaudal direction. In some examples, shunting cathodes may be used in MICC fashion to make anodic stimulation more localized (e.g., along rostro-caudal and medo-lateral direction). Because the rootlets span out at this point, the cathodes can be used to shunt away the anodic current from the rootlets that do not correspond to the rootlets of interest. In an example, a long rostro-caudal anodic monopole may be used to excite a larger region of the DREZ.

The selectable electrostimulation setting may include paresthesia-free stimulation modes, which generally may not cause paresthesia sensation during stimulation. Examples of the paresthesia-free stimulation modes include a Fast-Acting Sub-perception Therapy (FAST) mode, a Dorsal Horn Modulation (DHM) mode, a burst mode, and an Low-Rate Active Recharge (LRAR) mode. The FAST mode allows stimulation pulses to be delivered to provide profound paresthesia-free pain relief in a short time period (e.g., several minutes) by increasing surround inhibition. The DHM a stimulation mode that can target inhibitory interneurons over dorsal column fibers. Under the LRAR mode, sub-perception stimulation pulses are delivered at lower frequencies than the typical DHM frequencies.

In some examples, based on positions of lead placement, the stimulation mode circuit 1432 may generate multiple CPS. Each CPS represents a focal point of a stimulation field established by stimulation energy applied to the electrodes on a portion of an epidural lead. The stimulation fields corresponding to the multiple CPS may activate respective spinal neural targets at different spinal cord levels. To generate multiple CPS, the user may program respective plurality of electrodes on a lead with respective paresthesia-based or paresthesia-free stimulation modes and stimulation parameters. Examples of programming stimulation modes and parameters for electrodes on different portions of a lead to target multiple CPS are discussed below with reference to FIGS. 17A-17B.

The stimulation mode circuit 1432 may generate respective selectable electrostimulation settings for one or more of the contact groups generate by the neural target identifier 1431. The selectable electrostimulation settings for one contact group may be different from the selectable electrostimulation settings for another contact group. In an example, two different contact groups may have at least one common electrostimulation setting (e.g., anodic stimulation). In an example, the stimulation mode circuit 1432 may generate a plurality of candidate paresthesia-based stimulation modes and a plurality of candidate paresthesia-free stimulation modes for a contact group. A user may make a selection from the paresthesia-based stimulation modes and/or the paresthesia-free stimulation modes for the given contact group, via the user input unit 1411 of the user interface 1410. Based on the selected stimulation mode, the user may program one or more stimulation parameters, such as current amplitude or a voltage amplitude, a pulse width, a pulse shape (waveform), a pulse rate, or a duty cycle, among other parameters. The stimulation modes and stimulation parameters corresponding to a contact group may be stored in a storage device, such as the storage device 419 of the programming device 413. Examples of selecting a paresthesia-based stimulation mode or a paresthesia-free stimulation mode and programming stimulation parameters on a user interface are discussed below with reference to FIGS. 15C-15E and 16B-16D.

The stimulation controller 1433 may generate a control signal for adjusting the stimulation setting, such as by trolling the CPS location or tuning one or more stimulation parameters (e.g., pulse width, amplitude, duty cycle, stimulation rate, modulation frequency, modulation depth, etc.). The control signal may trigger the electrostimulator 1440 to deliver pain-relieving neuromodulation energy at the one or more lateral spinal neural targets, such as identified automatically by the neural target identifier 1431 or manually selected by the user, in accordance with the user selected electrostimulation setting, such as provided by the stimulation mode circuit 1432. The electrostimulator 1440 can be an implantable module, such as incorporated within the implantable system 521. Alternatively, the electrostimulator 1440 can be an external stimulation device, such as incorporated with the external system 522.

In some examples, the stimulation controller 1433 may control the electrostimulator 1440 to generate electrostimulation energy to stimulate, individually and independently, each of two or more identified lateral spinal neural targets in accordance with electrostimulation settings (e.g., stimulation modes and stimulation parameters) respectively determined or selected for the two or more identified lateral spinal neural targets. The patient may provide feedback, such as via the user interface 1410, on pain relief responsive to the electrostimulation at the two or more identified candidate neural targets. Based on the patient feedback, the stimulation controller 1433 may select an "optimal" neural target among the two or more identified candidate neural targets, such as one with the most significant pain relief effect. In some examples, the stimulation controller 1433 may rank the two or more identified candidate neural targets in an ascending order or a descending order of the pain relief effects. The electrostimulator 1440 may be programmed to deliver clinical pain therapy (e.g., a chronic pain stimulation) to the selected "optimal" neural target in accordance with the corresponding stimulation setting. The identified candidate neural targets and the optimal neural target, along with the corresponding stimulation modes and stimulation parameters, may be stored in a storage device, such as the storage device 419 of the programming device 413.

Depending on the selection of a paresthesia-based stimulation mode or a paresthesia-free stimulation mode, the pain-relieving neurostimulation may be supra-perception or sub-perception. The stimulation energy may be delivered using monophasic stimulation pulses applied to each electrode, which can be used as either an anode or cathode in accordance with the fractionalization configuration. Alternatively, the stimulation energy may be delivered using biphasic stimulation pulses. Each biphasic pulse has a first phase of a first polarity followed by a second phase of a second polarity opposite of the first polarity. The first and second phases can be symmetric (e.g., the same magnitude or duration). Alternatively, the first and second phases can be asymmetric. Because of opposite polarities of the two phases in a stimulation pulse, the electrode polarity (i.e., designation of an electrode as an anode or as a cathode) would flip when the stimulation current changes from the first phase to the second phase. In an example, the cathode and anode designation may be modified based on the first phase of the biphasic pulse. For example, if the first phase is positive, then no modification is made to the anode and cathode that have been determined. If the first phase is negative, then the anode and cathode designation are swapped. In an example, asymmetric biphasic stimulation may be delivered to both a preferred stimulation site and a site where stimulation is to be avoid. At the preferred stimulation site, the biphasic stimulation can include a first anodic phase with a longer duration and smaller magnitude, followed by a second cathodic phase with a shorter duration and larger magnitude. At the region to avoid, biphasic stimulation can include a first cathodic phase with a longer duration and smaller amplitude (sub-threshold for its pulse width), followed by a second anodic phase with a shorter duration and higher amplitude for charge balance.

Figure 15A:
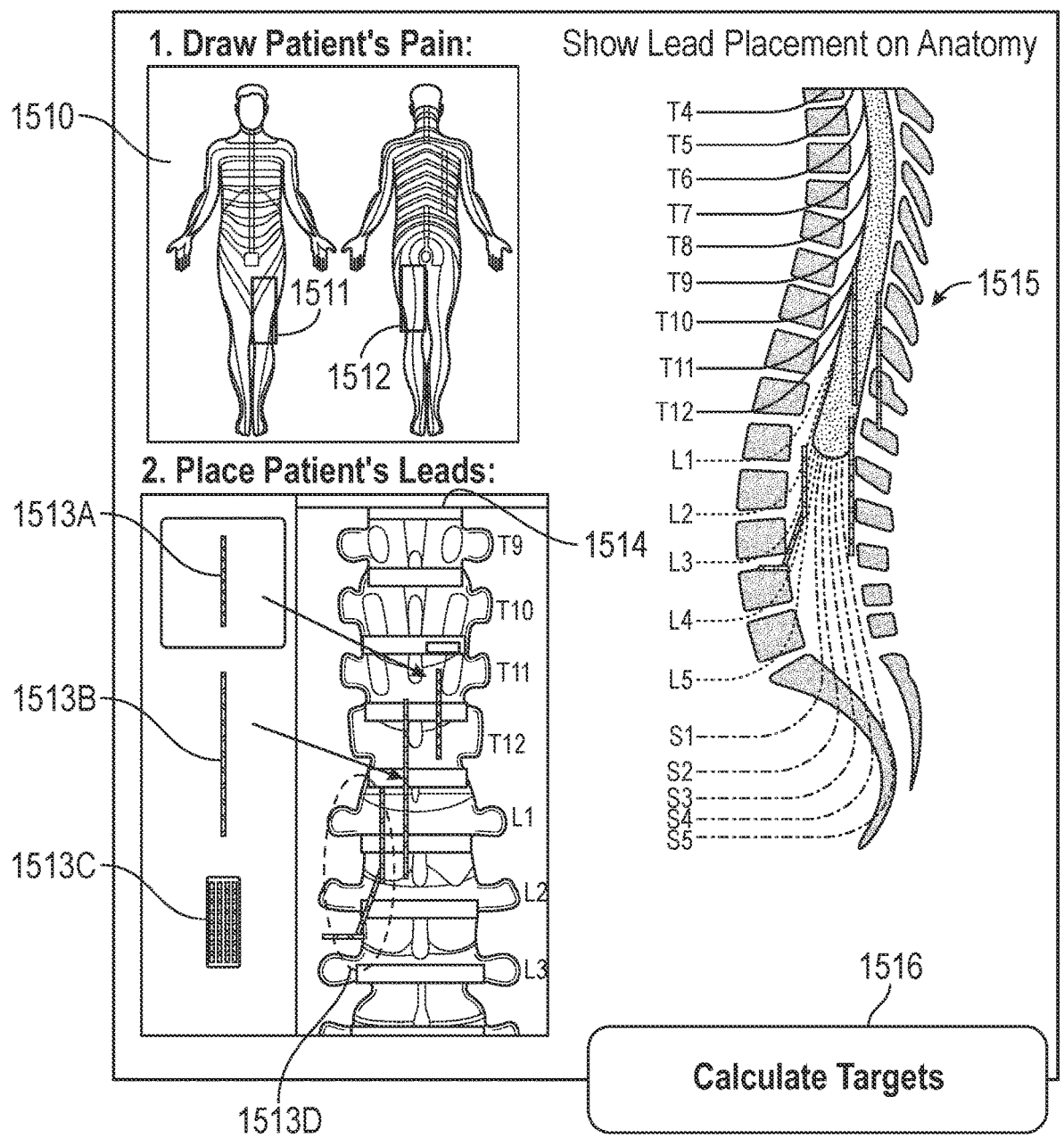
FIGS. 15A-15F illustrate, by way of example, a user interface for programming selectable lateral SCS for pain control.
Figure 15B:
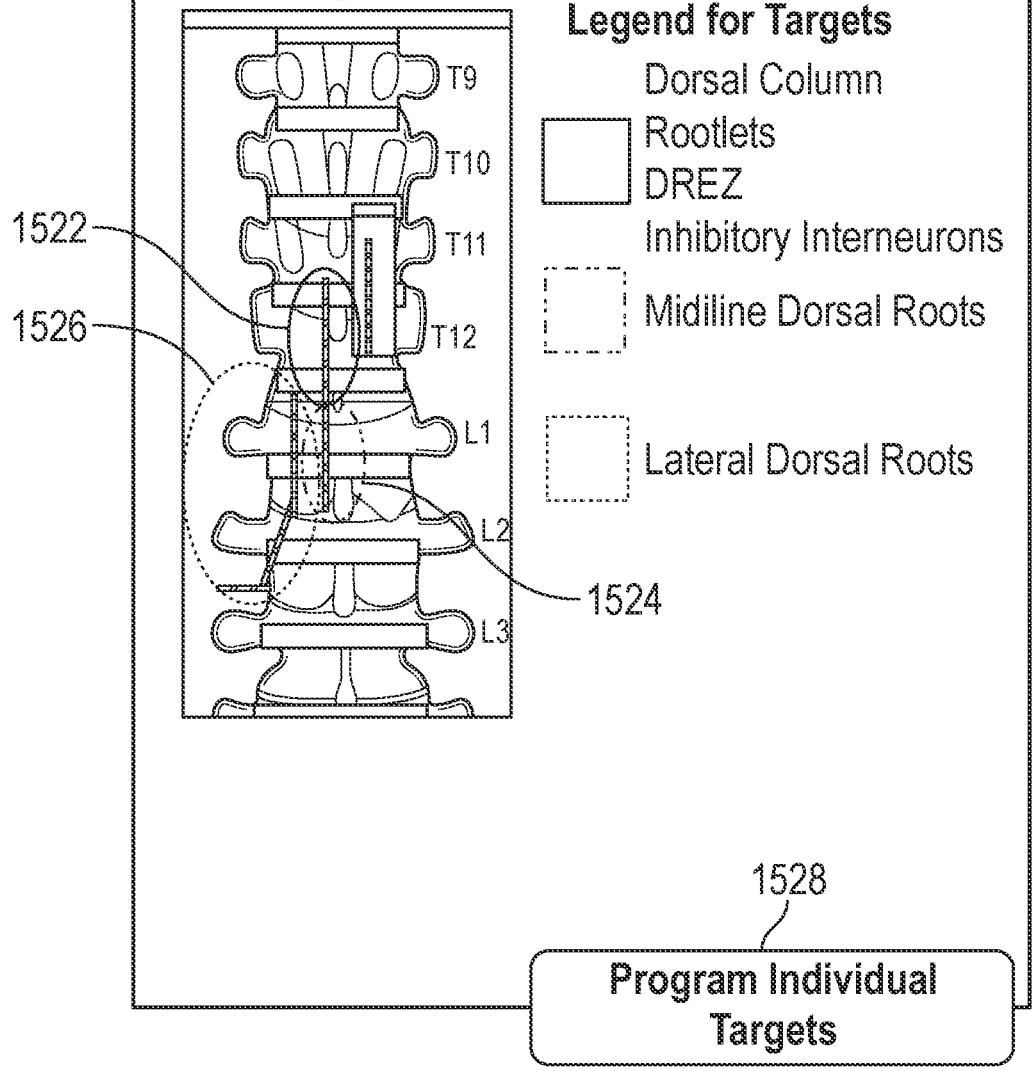

FIGS. 15A-15F illustrate, by way of example, a user interface for programming selectable lateral SCS for pain control. In FIG. 15A, pain drawings 1510 (similar to the pain drawings show in FIG. 12B) illustrating a human body diagram with patient-identified pain areas 1511 and 1512 may be provided by the user or the patient, such as by using UI controls on the user interface. Marking of dermatomes may be included in the human body diagram to provide a visually represent pain dermatomes corresponding to the patient-identified pain areas 1511 and 1512. The patient-identified pain area and the pain dermatomes may be used for identifying spinal neural targets and/or for generating a list of selectable electrostimulation settings such as stimulation modes. For this reason, the SCS programming method as described in FIGS. 15A-15F is also referred to as a "dermatomal mode". The user interface in FIG. 15A may also display one or more lead types with different size, length, shape, or electrode number and arrangement, such as a first type cylindrical lead 1513A, a second type cylindrical lead 1513B (longer and having more electrodes than the first type lead 1513A), and a paddle lead 1513C, among others. In some examples, two or more leads of the same or different types (e.g., a percutaneous lead, or a cylindrical lead) may be combined to form a curved lead 1513D. In an example, the curved lead 1513 comprises two or more cylindrical lead segments arranged at angles relative to each other. The curved lead 1513D may include multiple electrodes both laterally in the intervertebral foramen and in the epidural space. The curved lead 1513D may provide more efficient and focalized stimulation of lateral spinal neural targets with complex anatomy.

The user may select a lead type (such as by clicking on the lead image), and move or apply it to a desired location of a graphical spinal cord representation 1514. As an example, FIG. 15A illustrates placement of a first type cylindrical lead 1513A at levels T11-T12, a second type cylindrical lead 1513B at levels T12-L2, and a curved lead 1513D comprising three first type cylindrical leads 1513A concatenated with specific angles relative to each other that is placed at levels L1-L3. A drawing 1515 of all the leads placement on spinal cord anatomy may be displayed on the user interface.

FIG. 15B illustrates a user interface showing spinal neural targets automatically identified based on the user input of the pain areas on the pain drawings 1510 and the leads placements as shown in 1514 and 1515. The identification of spinal neural targets may be activated using a UI control button, such as by clicking on the "Calculate Targets" button 1516. The spinal neural targets may be identified by the neural target identifier 1431 of FIG. 14. As discussed above, the neural target identifier 1431 may generate one or more contact groups each comprising respective plurality of electrode-tissue contacts associated with electrodes on the same lead or two or more different leads. FIG. 15B illustrates, by way of example and not limitation, a first contact group 1522, a second contact group 1524, and a third contact group 1526. The contact groups may be distinguished by different colors or renders displayed on the user interface. For example, the first contact group 1522 may be shown in yellow, the second contact group 1524 may be shown in green, and the third contact group 1526 may be shown in blue. Each contact group includes lead electrode-tissue contacts targeting certain spinal neural targets at respective spinal cord levels. In the example as shown in FIG. 15B, the first contact group 1522 is located at T12-L1 levels, and targets dorsal column, dorsal rootlets, DREZ, a Lissauer's track, and inhibitory interneurons. The second contact group 1524 is at L1-L2 levels, and targets midline dorsal roots. The third contact group 1526 is at L1-L3 levels, and targets lateral dorsal roots. In some examples, the spinal neural targets for a contact group may be identified further based on a rostral-caudal position and/or a medio-lateral position of the contact group relative to the spinal cord level(s) innervating the pain dermatomes. Table 1 below shows examples of spinal neural targets identified for different contact groups depending on whether the electrode-tissue contacts of the contact group are at, or rostral or caudal to, the spinal cord level(s) that innervate the pain dermatomes.

TABLE 1

| Contact Groups | Contacts at the level of pain dermatomes | Contacts rostral or caudal to the level of pain dermatomes |
|---|---|---|
| First Contact Group | Rootlets, DREZ | Dorsal columns |
| Second Contact Group | Midline dorsal roots | None (i.e., no stimulation delivered) |
| Third Contact Group | Lateral dorsal roots | None (i.e., no stimulation delivered) |

Figure 15C:
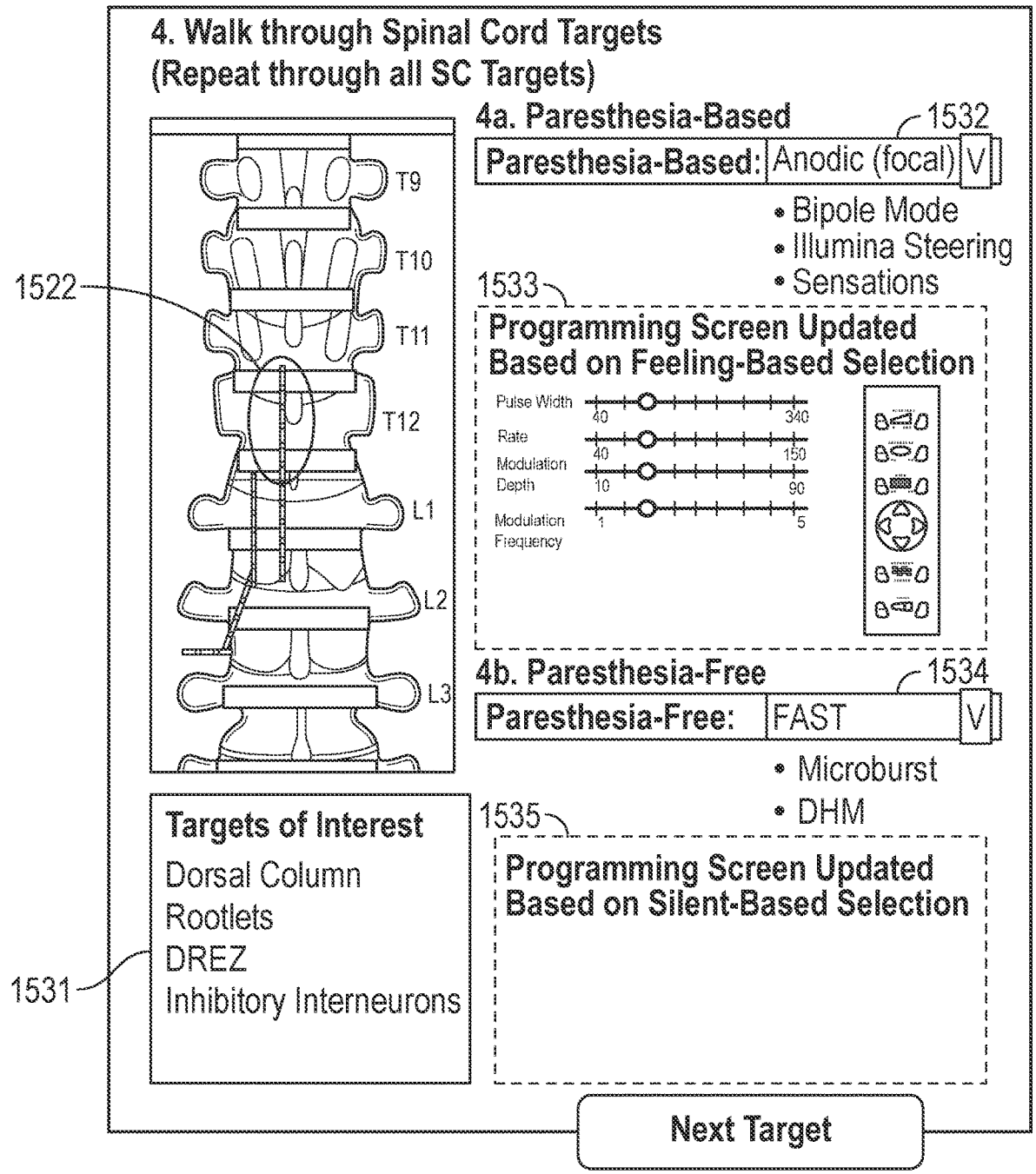
Figure 15D:
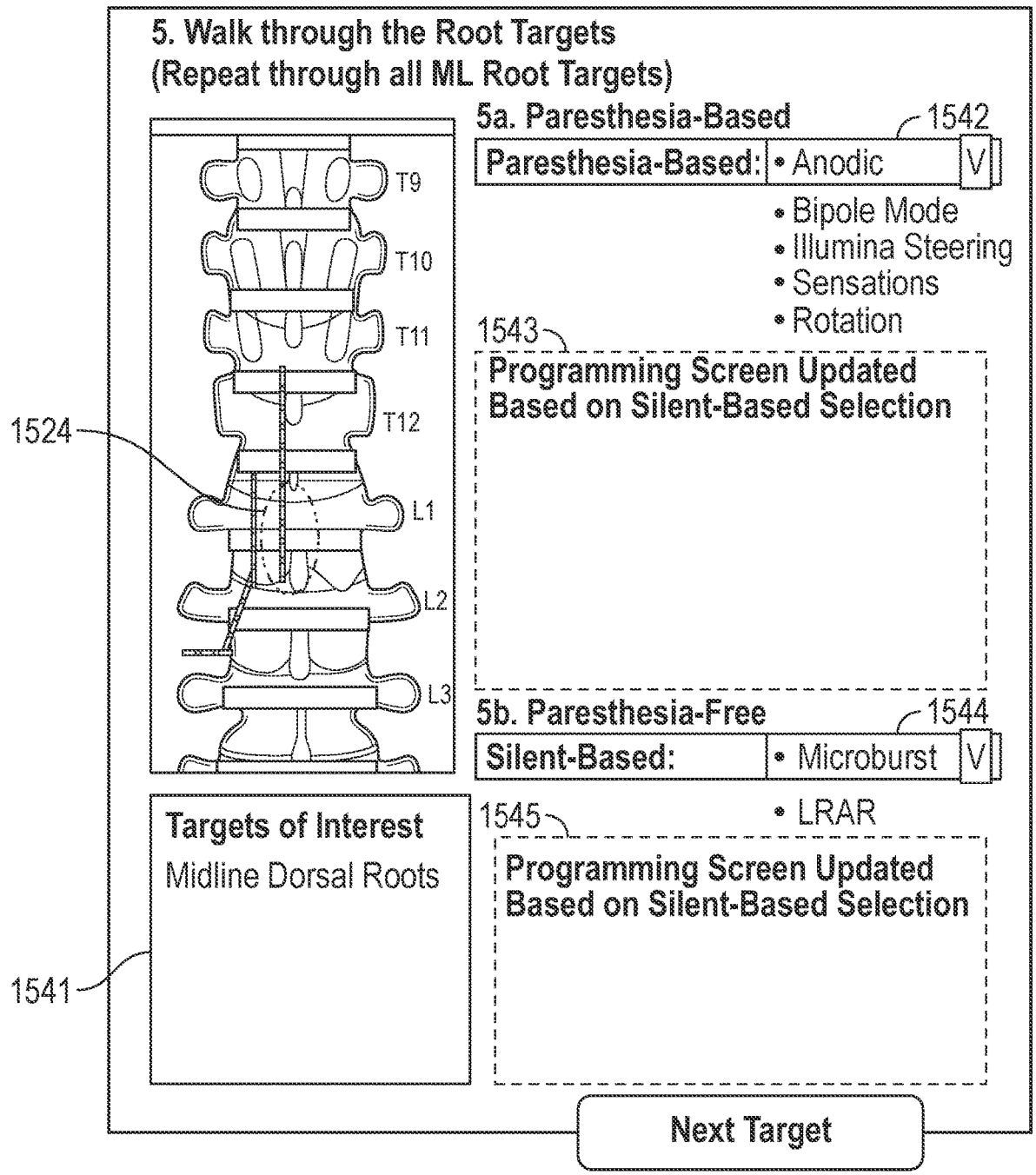
Figure 15E:
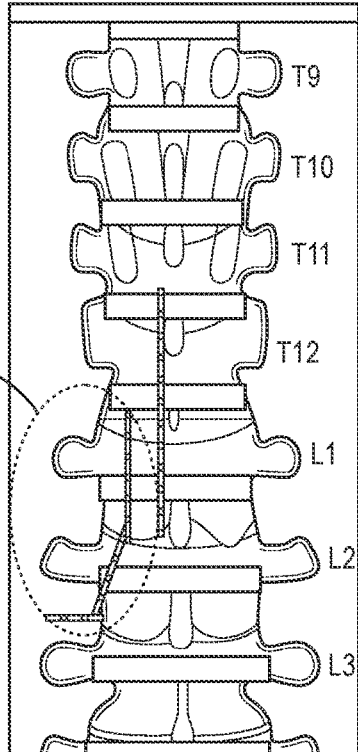

A user may then program electrostimulation therapy for individual targets in each contact group, such as by clicking on the "Program Individual Targets" button 1528. FIGS. 15C-15E illustrate programming screens for programming therapies for the neural targets associated with the first, second, and third contact groups, respectively. Targets of interest, which are automatically identified by the neural target identifier 1431 based on user input of leads placement and pain drawings and the associated pain dermatomes, may be displayed on the user interface. FIG. 15C illustrates the neural targets 1531 identified for the first contact group, FIG. 15D illustrates the neural targets 1541 identified for the second contact group, and FIG. 15E illustrates the neural targets 1551 identified for the third contact group. To program an electrostimulation therapy for a neural target of a contact group, the user may select a stimulation mode from a paresthesia-based stimulation mode drop-down menu 1532, or from a paresthesia-free stimulation mode drop-down menu 1534, as shown in FIG. 15C for the first contact group. The user may similarly select a stimulation mode for neural targets associated with the second contact group from a paresthesia-based stimulation mode drop-down menu 1542 or a paresthesia-free stimulation mode drop-down menu 1544 as shown in FIG. 15D, or select a stimulation mode for neural targets associated with the third contact group from a paresthesia-based stimulation mode drop-down menu 1552 or a paresthesia-free stimulation mode drop-down menu 1554 as shown in FIG. 15E. The drop-down menus 1532, 1534, 1542, 1544, 1552, and 1554 each include a list of selectable candidate stimulation modes for the present contact group. Table 2 below shows examples of candidate paresthesia-base stimulation modes and candidate paresthesia-free stimulation modes for different contact groups. In this table and throughout this document, Anodic (Focal) stimulation is mode designed to excite neural targets that are perpendicular to the lead. Steering mode refers to a steering algorithm. Rotation refers to a stimulation mode designed to better target fibers that run diagonal to the rostro-caudal axis of the spinal cord. FAST mode allows stimulation pulses to be delivered to provide profound paresthesia-free pain relief in a short time period (e.g., several minutes) by increasing surround inhibition. DHM a stimulation mode that can target inhibitory interneurons over dorsal column fibers. LRAR mode refers to sub-perception stimulation pulses delivered at lower frequencies than the typical DHM frequencies. The stimulation mode circuit 1432 may generate the drop-down menus based on Table 2.

TABLE 2

| Contact Groups | Paresthesia-based stimulation modes | Paresthesia-free stimulation modes |
| --- | --- | --- |
| First Contact Group | Anodic (Focal) stim<br>Bipole Mode<br>Steering<br>Sensations | FAST<br>Microburst<br>DHM |
| Second Contact Group | Anodic (Focal) stim<br>Bipole Mode<br>Steering<br>Sensations<br>Rotation | Microburst<br>LRAR |
| Third Contact Group | Bipole Mode<br>Steering<br>Sensations | FAST<br>Microburst<br>DHM |

Based on the user selection of a paresthesia-based stimulation mode or a paresthesia-based stimulation mode, a programming screen may be displayed. In some examples, as illustrated in FIGS. 15C-15E, separate programming screens may be shown for the user-selected paresthesia-based stimulation mode and for the user-selected paresthesia-free stimulation mode, such as programming screens 1533, 1543, and 1553 for the paresthesia-based stimulation mode, and programming screens 1535, 1545, and 1555 for the paresthesia-based stimulation mode. The programming screens may prompt the user to provide, and receive therefrom, stimulation parameters (e.g., pulse width, amplitude, duty cycle, stimulation rate, modulation frequency, modulation depth, etc.) for the stimulation mode at identified neural targets associated with the present contact groups.

Figure 15F:
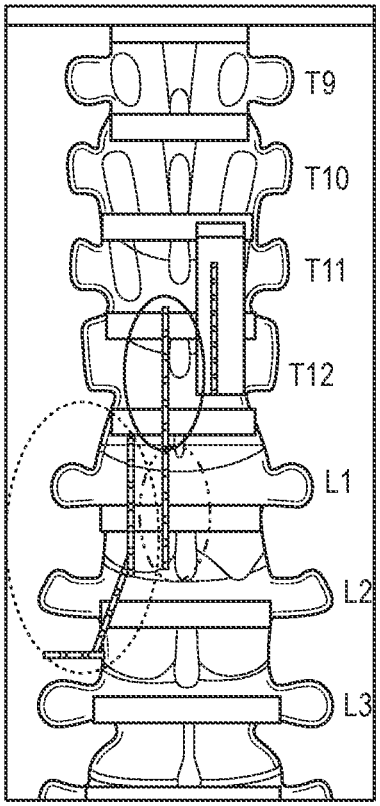

In some examples, the user may select multiple candidate neural targets and program corresponding neurostimulation therapies. The programmed therapy (including the stimulation mode and the stimulation parameters) for a particular neural target is referred to as a "program". FIG. 15F illustrates a summary report 1560 displayed on the user interface, which includes the identified lateral spinal neural targets and corresponding electrostimulation stimulation settings (e.g., stimulation modes), organized as numerically labeled programs. In this example, five programs are shown. Programs 1 and 2 are associated with the first contact group, programs 3 and 4 are associated with the second contact group, and program 5 is associated with the third contact group. Test electrostimulation energy may be independently delivered to the patient in accordance with each of the five programs. The patient may provide feedback about pain relief responsive to the electrostimulation. An "optimal" neural target with the associated program may be identified, such as one with the most significant pain relief effect. For example, if the patient indicates that program 3 results in the most significant pain relief effect, then the user (e.g., physician) can immediately tell from the summary report details of program 3 (in this case, electrostimulation delivered at the second contact group using a burst mode to target dorsal roots). The electrostimulator may be programmed to deliver clinical pain therapy (e.g., a chronic pain stimulation) at the neural target using the corresponding stimulation setting in accordance with program 3. In some examples, the programs (and associated neural targets) may be ranked in an ascending order or a descending order of the pain relief effects.

FIGS. 16A-16D illustrate, by way of example, a user interface for programming selectable lateral SCS for pain control. Compared to the "dermatomal mode" of SCS programming (as described above with reference to FIGS. 15A-15F) where the neural targets are automatically identified for each contact group based on the user input of pain drawings and leads placements, FIGS. 16A-16D illustrate a "manual mode" of SCS programming, in which the user may manually select a neural target from selectable candidate spinal neural targets. The user may manually select the target based on the placement of the at least one lead, usable electrodes from impedance measures, patient-specific anatomy, instructions from the physician, etc.

Figure 16A:
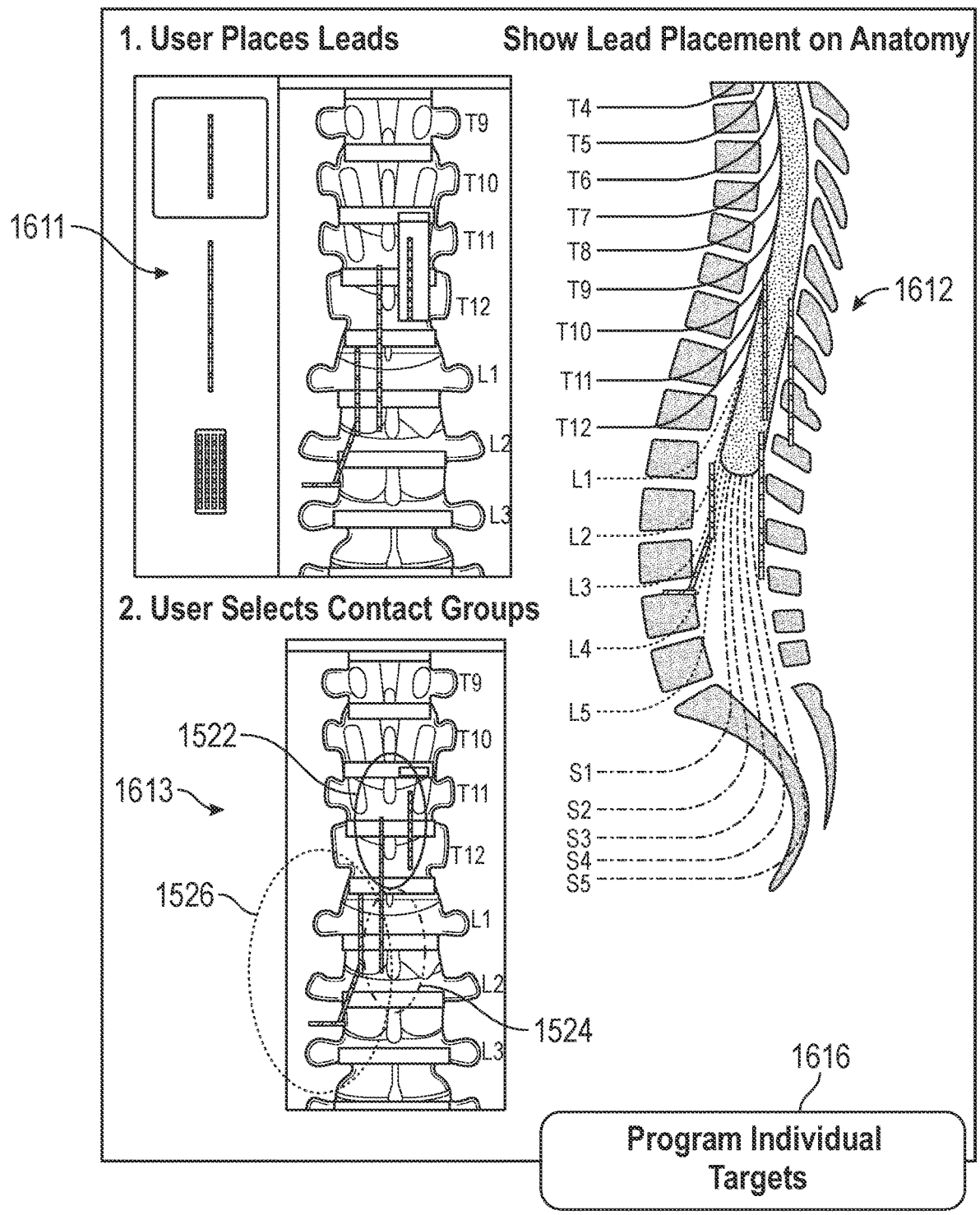

FIG. 16A illustrates a lead placement screen 1611, similar to the leads placement as shown in FIG. 15A. A pain drawing and/or pain dermatomes may or may not be provided in the manual mode. Once the leads placement is completed, a drawing 1612 of the lead placement on spinal cord anatomy, similar to the drawing 1515, may be displayed on the user interface. Also shown in FIG. 15A are one or more contact groups each comprising respective plurality of tissue contacts associated with electrodes on the same lead or two or more different leads, such as contact groups 1522, 1524, and 1526.

Figure 16C:
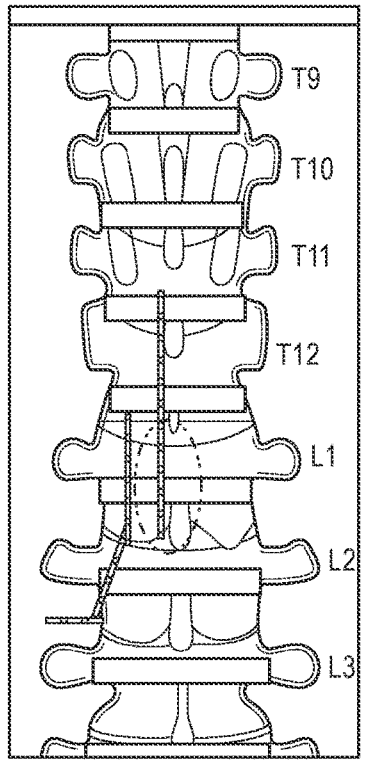

The user may select a contact group (e.g., the first contact group 1522), and program electrostimulation therapy for one or more targets associated with the selected contact group using UI controls on the user interface, such as by clicking on the "Program Individual Targets" button 1616. FIGS. 16B-16D illustrate programming screens where a user may select a neural target from a list of selectable candidate spinal neural targets associated with the first, second, and third contact groups, respectively. The selectable candidate spinal neural targets, such as a candidate target list 1621 for the first contact group, a candidate target list 1631 for the second contact group, and a candidate target list 1641 for the third contact group, may include candidate targets at the level of spinal cord where the contact group is located. In an example as illustrated in FIGS. 16B-16D, the same candidate target list is provided for different contact groups, including dorsal column, dorsal horn, DREZ, a Lissauer's track, rootlets, and dorsal roots. However, it is to be noted that the candidate targets are in reference to the spinal cord level(s) of the respective contact groups. For example, the "dorsal roots" for the first contact group 1522 are dorsal roots at T12-L1 levels, while the "dorsal roots" for the second contact group 1524 are dorsal roots at L1-L2 levels.

To program an electrostimulation setting for a user selected neural target of a specific contact group (e.g., "dorsal roots" in the candidate target list 1621 for the first contact group), the user may select a stimulation mode from a paresthesia-based stimulation mode drop-down menu 1622, or from a paresthesia-free stimulation mode drop-down menu 1624, as shown in FIG. 16B for the first contact group. The user may similarly determine a stimulation mode for neural targets associated with the second contact group by selecting from a paresthesia-based stimulation mode drop-down menu 1632 or a paresthesia-free stimulation mode drop-down menu 1634 as shown in FIG. 16C, or determine a stimulation mode for neural targets associated with the third contact group by selecting from a paresthesia-based stimulation mode drop-down menu 1642 or a paresthesia-free stimulation mode drop-down menu 1644 as shown in FIG. 16D. The drop-down menus 1622, 1624, 1632, 1634, 1642, and 1644 each include a list of selectable candidate stimulation modes for the present contact group. Table 3 below shows examples of candidate paresthesia-base stimulation modes and candidate paresthesia-free stimulation modes for different contact groups, which may be used to generate respective drop-down menus.

TABLE 3

| Candidate Targets | Paresthesia-based therapy options | Paresthesia-free therapy options |
| --- | --- | --- |
| Dorsal Column | Bipolar mode Steering Sensations | FAST Pulse Width Modulation Rate Modulation |
| Dorsal Horn | None | DHM |
| DREZ | Anodic Long Anodic | Microburst (over anodic/ long anodic sweet spot) |
| Rootlets | Anodic Rotational Target Pole | Microburst LRAR (Applied over paresthesia sweet spot) |
| Dorsal Roots | Dermatome-specific target pole Rotational target pole Dorsal Root steerable space Root selectivity | Microburst LRAR (Applied over paresthesia sweet spot) |

Similar to the programming screens shown in FIGS. 15C-15E, separate programming screens may be shown for the user-selected paresthesia-based stimulation mode (e.g., the programming screens 1623, 1633, and 1643) and the user-selected paresthesia-free stimulation mode (e.g., the programming screens 1625, 1635, and 1645). The programming screens may prompt the user to provide, and receive therefrom, stimulation parameters (e.g., pulse width, amplitude, duty cycle, stimulation rate, modulation frequency, modulation depth, etc.) for the stimulation mode at user selected neural targets associated with the present contact groups. The identified lateral spinal neural targets and corresponding electrostimulation stimulation settings (e.g., stimulation modes), organized as numerically labeled programs, may be displayed, as discussed above with reference to FIG. 15F. Test electrostimulation energy may be independently delivered to the patient in accordance with each of the programs, and an "optimal" neural target with the associated program may be identified based on patient feedback about pain relief responsive to the electrostimulation. The user may the program the electrostimulator to deliver clinical pain therapy (e.g., a chronic pain stimulation) in accordance with the selected optimal program.

Figure 17B:
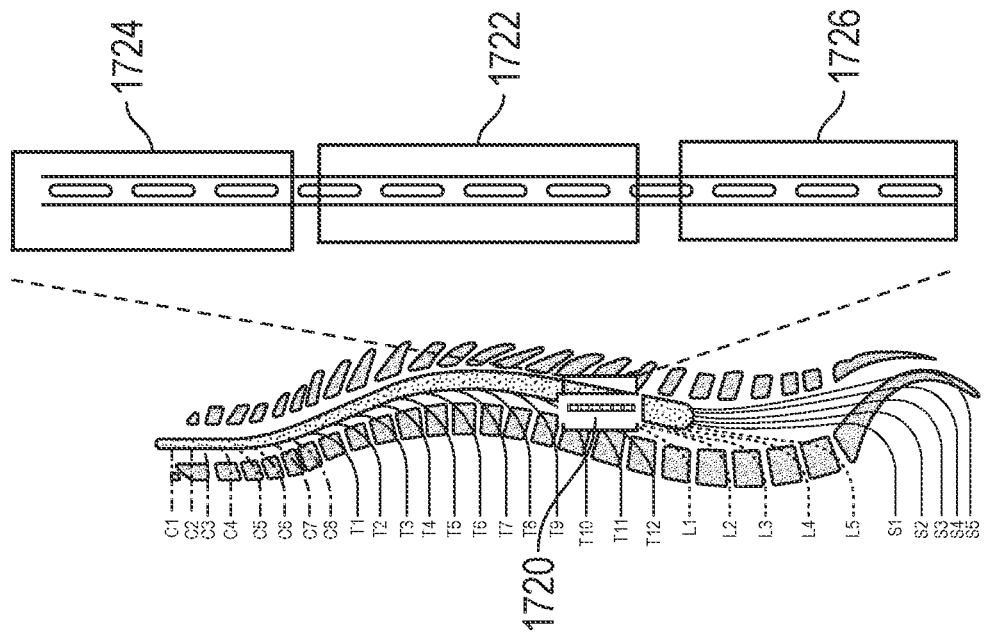
FIGS. 17A-17B illustrate, by way of example, a user interface for programming SCS to target multiple Central Points of Stimulation (CPS) using electrodes on different portions of an epidural lead.
Figure 17A:
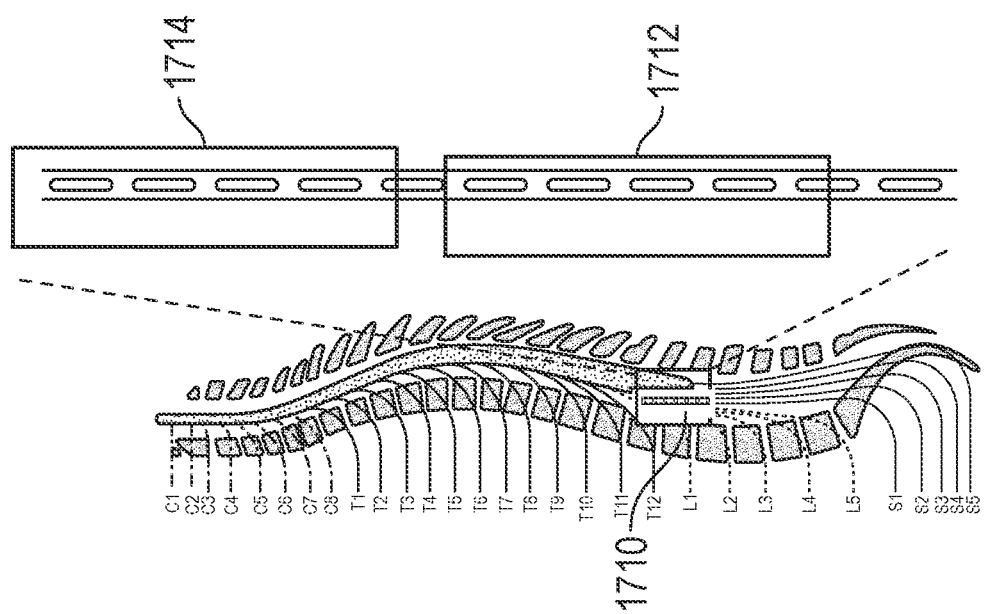

FIGS. 17A-17B illustrate, by way of example and not limitation, a user interface for programming SCS to target multiple Central Points of Stimulation (CPS) using electrodes on different portions of a lead placed in a vicinity of a lateral portion of the spinal cord. In FIG. 17A, an epidural lead 1710 is placed at T12-L2 levels to deliver electrostimulation to help alleviate knee pain. Monopolar anodic stimulation may be applied to electrodes on a first lead segment 1712 to target terminals because the electrode-tissue contacts in this area are in the region of L3-4 DREZ (including terminals from the rootlets). Additionally, bipolar stimulation may be applied to electrodes on a second lead segment 1714 (which is rostral to the first lead segment 1712) to target dorsal column because the electrode-tissue contacts in this area are above the DREZ of the L3-L4 fibers. In FIG. 17B, an epidural lead 1720 is placed at T10-T12 levels to deliver electrostimulation to help alleviate pelvic pain. Monopolar anodic stimulation may be applied to electrodes on a first lead segment 1722 to target terminals because the electrode-tissue contacts in this area are in the region of L1-L2 DREZ (including terminals from the rootlets). Bipolar stimulation may be applied to electrodes on a second lead segment 1724 (which is rostral to the first lead segment 1722) to target dorsal column because the electrode-tissue contacts in this area are above the DREZ of the L1-L2 fibers. Bipolar or tripolar stimulation may be applied to electrodes on a third lead segment 1726 (which is caudal to the first lead segment 1722) to target dorsal roots because the electrode-tissue contacts in this area are blow the DREZ of the L1-L2 fibers.

Figure 18:
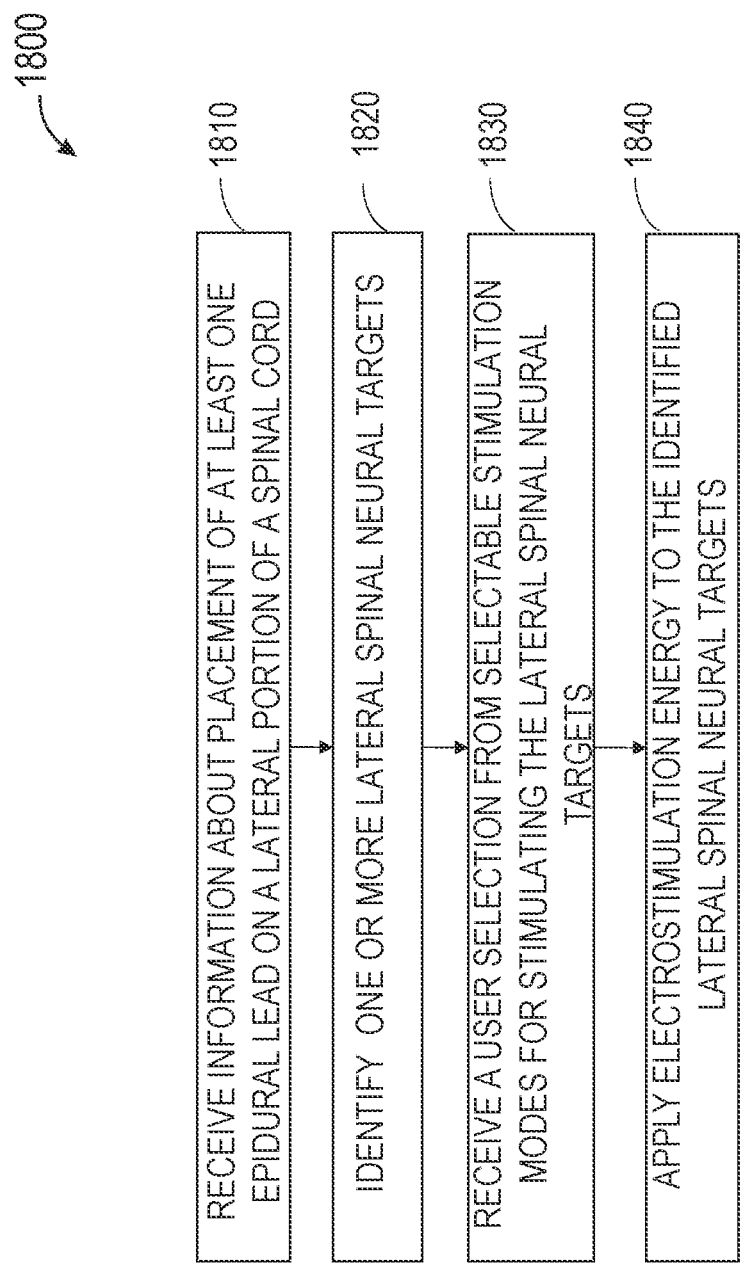
FIG. 18 is a flow chart illustrating, by way of example, a method for programming and applying selectable lateral SCS for pain control.

FIG. 18 is a flow chart illustrating, by way of example and not limitation, a method 1800 for programming and applying selectable lateral SCS for pain control. The method 1800 may be carried out using a medical system such as one of the neuromodulation systems 210 or 1400. Portions of the method 1800 may be implemented in an external device, such as a device in the external system 522, or one of the programming devices 213 or 413, the CP 629, or the RC 628. By executing the method 1800, the programming device or the external device may program a neuromodulation device (e.g., one of the neuromodulation devices 212, 312 or 512, or the IPG 627, or the electrostimulator 1440) to deliver stimulation to various spinal neural targets, such as one or more of spinal nerves, dorsal roots, dorsal root ganglia, among others.

At 1810, information about placement of at least one lead in a vicinity of a lateral portion of a spinal cord can be received from a user via a user interface, such as the user interface 1410. On the user interface, the user may select a lead type from a plurality of available lead types including, for example, percutaneous cylindrical leads, linear paddles, multiple-column paddles, or directional leads with segmented electrodes, and place the selected lead at a desired location of a graphical spinal cord representation displayed on the user interface. For example, the user may place a selected lead at a lateral portion of particular spinal cord levels. Each selected lead comprises an array of electrodes interfacing with the graphical spinal cord representation at respective electrode-tissue contacts. In some examples, multiple leads may be selected and placed at respective locations of the graphical spinal cord representation.

At 1820, one or more lateral spinal neural targets may be identified based on the lead placement information. The lateral spinal neural targets may be automatically identified, such as using the neural target identifier 1431. Alternatively, the lateral spinal neural targets may be manually selected from a list of pre-generated candidate neural targets displayed on the user interface, as illustrated in FIGS. 16B-16D. The electrode-tissue contacts may be grouped into one or more contact groups. A contact group comprises a plurality of electrode-tissue contacts associated with electrodes on the same lead or two or more different leads. Spinal neural targets at respective spinal cord levels may be identified for each of the contact groups. FIG. 15B illustrates an example of three automatically generated contact groups each comprising electrode-tissue contacts targeting one or more spinal neural targets. The contact groups may be distinguishably displayed in different colors or renders on the user interface.

In some examples, the identification of one or more neural targets for a contact group may further be based on patient pain data, such as user input of pain area(s) or pain dermatome(s), as illustrated in FIG. 15A. A rostral-caudal position and/or a medio-lateral position of a contact group relative to spinal cord level(s) innervating the pain dermatomes may be determined based on the lead placement information. Spinal neural targets may be identified for a contact group depending on whether the electrode-tissue contacts of the contact group are at, or being rostral or caudal to, the spinal level of pain dermatomes, as shown in Table 1.

At 1830, a user may make a selection from a plurality of selectable stimulation modes for stimulating the identified lateral spinal neural targets. The selectable electrostimulation modes may include paresthesia-based stimulation modes and paresthesia-free stimulation modes. Paresthesia-based stimulation can cause paresthesia sensation during stimulation. Examples of the paresthesia-based stimulation modes include a monopolar stimulation mode, a bipolar stimulation mode a tripolar stimulation mode, asteering mode, a sensations mode, and a rotation mode, among others. The stimulation may be cathodic or anodic. The paresthesia-free stimulation modes generally may not cause paresthesia sensation during stimulation. Examples of the paresthesia-free stimulation modes include a FAST mode, a DHM mode, a burst mode, and an LRAR mode, among others. In an example, a plurality of recommended paresthesia-based stimulation modes and a plurality of candidate paresthesia-free stimulation modes may be generated for each contact group. The user may select a paresthesia-based stimulation mode and/or a paresthesia-free stimulation mode for the given contact group. The user may then program one or more stimulation parameters, such as current amplitude or a voltage amplitude, a pulse width, a pulse shape (waveform), a pulse rate, or a duty cycle, among other parameters.

In some examples, based on positions of leads placement, multiple Central Points of Stimulation (CPS) may be generated, such as by the stimulation mode circuit 1432. Each CPS represents a focal point of a stimulation field established by stimulation energy applied to a plurality of electrodes on a portion of an epidural lead. The stimulation fields corresponding to the multiple CPS may activate respective spinal neural targets at different spinal cord levels. To generate multiple CPS, the user may program respective plurality of electrodes on a lead with respective paresthesia-based or paresthesia-free stimulation modes and stimulation parameters, as discussed above with reference to FIGS. 17A-17B.

At 1840, clinical electrostimulation energy may be applied to the selected neural target in accordance with the corresponding stimulation mode. In some examples, two or more lateral spinal neural targets may be automatically identified or manually selected at 1820. Electrostimulation energy may be delivered to stimulate, individually and independently, each of two or more identified lateral spinal neural targets in accordance with stimulation modes and stimulation parameters respectively determined or selected for the two or more identified lateral spinal neural targets. The patient may provide feedback on pain relief responsive to the electrostimulation at the two or more identified candidate neural targets. Based on the patient feedback, an "optimal" neural target may be selected from the two or more identified candidate neural targets, such as the one with most significant pain reduction. Clinical pain therapy (e.g., a chronic pain stimulation) may then be delivered at the selected "optimal" neural target in accordance with the corresponding stimulation setting. The identified candidate neural targets and the optimal neural target, along with the corresponding stimulation modes and stimulation parameters, may be stored in a storage device, such as the storage device 419 of the programming device 413.

Figure 19:
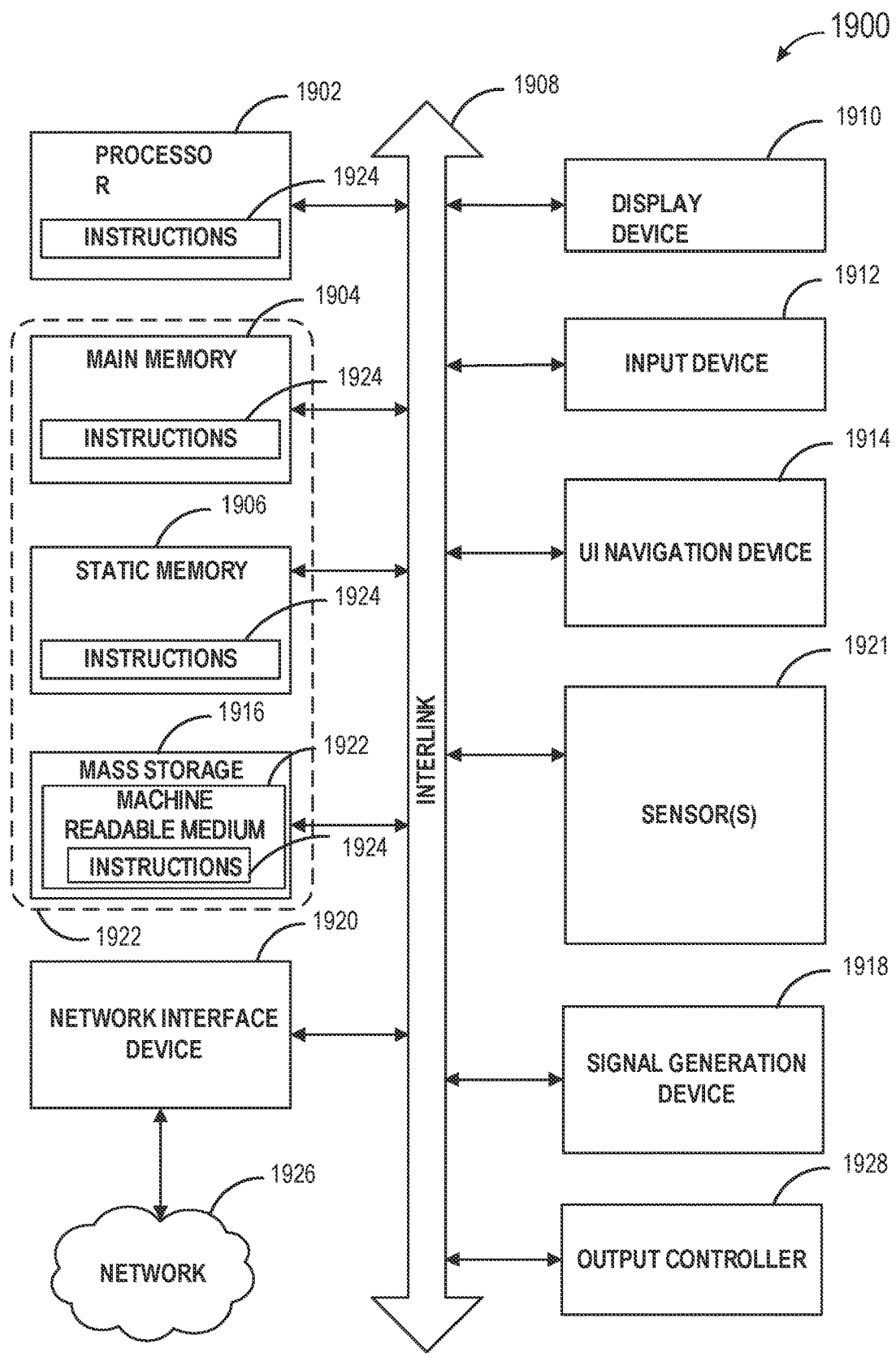
FIG. 19 illustrates generally a block diagram of an example machine 1900 upon which any one or more of the techniques (e.g., methodologies) discussed herein may perform.

FIG. 19 illustrates generally a block diagram of an example machine 1900 upon which any one or more of the techniques (e.g., methodologies) discussed herein may perform. Portions of this description may apply to the computing framework of various portions of the neuromodulation device or the external programming device.

In alternative embodiments, the machine 1900 may operate as a standalone device or may be connected (e.g., networked) to other machines. In a networked deployment, the machine 1900 may operate in the capacity of a server machine, a client machine, or both in server-client network environments. In an example, the machine 1900 may act as a peer machine in peer-to-peer (P2P) (or other distributed) network environment. The machine 1900 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1900 may include a hardware processor 1902 (e.g., a central processing unit (CPU), a graphics processing unit (GPU), a hardware processor core, or any combination thereof), a main memory 1904 and a static memory 1906, some or all of which may communicate with each other via an interlink (e.g., bus) 1908. The machine 1900 may further include a display unit 1910 (e.g., a raster display, vector display, holographic display, etc.), an alphanumeric input device 1912 (e.g., a keyboard), and a user interface (UT) navigation device 1914 (e.g., a mouse). In an example, the display unit 1910, input device 1912 and UI navigation device 1914 may be a touch screen display. The machine 1900 may additionally include a storage device (e.g., drive unit) 1916, a signal generation device 1918 (e.g., a speaker), a network interface device 1920, and one or more sensors 1921, such as a global positioning system (GPS) sensor, compass, accelerometer, or other sensors. The machine 1900 may include an output controller 1928, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1916 may include a machine readable medium 1922 on which is stored one or more sets of data structures or instructions 1924 (e.g., software) embodying or utilized by any one or more of the techniques or functions described herein. The instructions 1924 may also reside, completely or at least partially, within the main memory 1904, within static memory 1906, or within the hardware processor 1902 during execution thereof by the machine 1900. In an example, one or any combination of the hardware processor 1902, the main memory 1904, the static memory 1906, or the storage device 1916 may constitute machine readable media.

While the machine-readable medium 1922 is illustrated as a single medium, the term "machine readable medium" may include a single medium or multiple media (e.g., a centralized or distributed database, and/or associated caches and servers) configured to store the one or more instructions 1924.

The term "machine readable medium" may include any medium that is capable of storing, encoding, or carrying instructions for execution by the machine 1900 and that cause the machine 1900 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1924 may further be transmitted or received over a communication network 1926 using a transmission medium via the network interface device 1920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1920 may include one or more physical jacks (e.g., Ethernet, coaxial, or phone jacks) or one or more antennas to connect to the communication network 1926. In an example, the network interface device 1920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1900, and includes digital or analog communications signals or other intangible medium to facilitate communication of such software.

Various embodiments are illustrated in the figures above. One or more features from one or more of these embodiments may be combined to form other embodiments.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing spinal cord electrostimulation for pain control in a patient, the system comprising:
 a programming device configured to:
  receive information about placement of at least one lead in a vicinity of a lateral portion of a spinal cord;
  define one or more electrode-tissue contact groups on the lateral portion of the spinal cord, the one or more contact groups each comprising one or more lateral spinal neural targets identified and grouped based on the information about placement of at least one lead; and
  receive a user selection from selectable stimulation modes for stimulating the identified one or more lateral spinal neural targets of at least one of the one or more contact groups; and
 an electrostimulator configured to apply electrostimulation energy to the identified one or more lateral spinal neural targets via the at least one lead in accordance with the user selection from the selectable stimulation modes.

2. The system of claim 1, wherein the one or more lateral spinal neural targets of at least one of the one or more contact groups include at least one of a dorsal root entry zone, a Lissauer's track, a dorsal root, a dorsal rootlet, or a dorsal root ganglion.

3. The system of claim 1, wherein the one or more contact groups include at least one of:
- a first contact group comprising first lateral spinal neural targets, including dorsal column, dorsal rootlets, a dorsal root entry zone, a Lissauer's track, and inhibitory interneurons;
- a second contact group comprising second lateral spinal neural targets, including one or more midline dorsal roots; or
- a third contact froup comprising third lateral spinal neural targets, including one or more lateral dorsal roots.

4. The system of claim 1, wherein the programming device is configured to:
- receive information about pain area on patient body, the pain area corresponding to one or more dermatomes; and
- identify the one or more lateral spinal neural targets for at least one of the one or more contact groups further based on a rostral-caudal position or a medio-lateral position of the at least one contact group relative to spinal cord levels innervating the one or more dermatomes corresponding to the pain area.

5. The system of claim 1, wherein the programming device is configured to:
- for each of the one or more contact groups, receive a user selection from candidate spinal neural targets; and
- provide selectable stimulation modes for the user selected candidate spinal neural target.

6. The system of claim 5, wherein the candidate spinal neural targets include one or more of:
- a dorsal column;
- a dorsal horn;
- a Lissauer's track;
- a dorsal root entry zone;
- a dorsal rootlet;
- a dorsal root; or
- a dorsal root ganglion.

7. The system of claim 1, wherein the selectable stimulation modes include one or more candidate paresthesia-based stimulation modes and one or more candidate paresthesia-free stimulation modes.

8. The system of claim 1, wherein:
- the electrostimulator is configured to apply test electrostimulation energy to two or more identified lateral spinal neural targets individually and independently in accordance with corresponding stimulation modes respectively selected for the two or more identified lateral spinal neural targets; and
- the programming device is configured to select one of the two or more identified lateral spinal neural targets based on a patient feedback on pain relief responsive to the electrostimulation individually and independently applied to the two or more identified lateral spinal neural targets;
- wherein the electrostimulator is configured to apply clinical electrostimulation energy to the selected neural target in accordance with a corresponding stimulation mode.

9. The system of claim 8, comprising a display configured to display the two or more identified lateral spinal neural targets and the stimulation modes respectively selected for the two or more identified lateral spinal neural targets,
- wherein the programming device is configured to receive a user selection of one of the two or more identified lateral spinal neural targets based on the patient feedback on pain relief responsive to the electrostimulation individually and independently applied to each of the two or more identified lateral spinal neural targets.

10. The system of claim 1, wherein the programming device is configured to receive the user selection from the selectable stimulation modes including:
- a monopolar anodic stimulation mode applied to a first electrode set of the at least one lead to stimulate a dorsal root entry zone at a spinal cord level; and
- a bipolar stimulation mode applied to a second electrode set of the at least one lead to stimulate a dorsal column or a dorsal root at the spinal cord level.

11. A non-transitory machine-readable storage medium that includes instructions that, when executed by one or more processors of a machine, cause the machine to perform operations comprising:
- receiving information about placement of at least one lead in a vicinity of a lateral portion of a spinal cord of a patient;
- defining one or more lead electrode-tissue contact groups on the lateral portion of the spinal cord, the one or more contact groups each comprising one or more lateral spinal neural targets identified and grouped based on the information about placement of at least one lead;
- receiving a user selection from selectable stimulation modes for stimulating the identified one or more lateral spinal neural targets of at least one of the one or more contact groups; and
- applying electrostimulation energy to the identified one or more lateral spinal neural targets via the at least one lead in accordance with the user selection from the selectable stimulation modes.

12. The non-transitory machine-readable storage medium of claim 11, wherein the one or more lateral spinal neural targets of at least one of the one or more contact groups include at least one of a dorsal root entry zone, a Lissauer's track, a dorsal root, a dorsal rootlet, or a dorsal root ganglion.

13. The non-transitory machine-readable storage medium of claim 11, wherein the instructions cause the machine to perform operations further comprising receiving information about pain area on patient body, the pain area corresponding to one or more dermatomes, and
- wherein the the one or more lateral spinal neural targets for at least one of the one or more contact groups is identified further based on a rostral-caudal position or a medio-lateral position of the at least one contact group relative to spinal cord levels innervating the one or more dermatomes corresponding to the pain area.

14. The non-transitory machine-readable storage medium of claim 11, wherein the selectable stimulation modes include one or more candidate paresthesia-based stimulation modes and one or more candidate paresthesia-free stimulation modes.

15. The non-transitory machine-readable storage medium of claim 1 wherein the instructions cause the machine to perform operations further comprising:
- applying test electrostimulation energy to two or more identified lateral spinal neural targets individually and independently in accordance with corresponding stimulation modes respectively selected for the two or more identified lateral spinal neural targets;
- selecting one of the two or more identified lateral spinal neural targets based on a patient feedback on pain relief responsive to the electrostimulation individually and independently applied to the two or more identified lateral spinal neural targets; and applying clinical electrostimulation energy to the selected neural target in accordance with a corresponding stimulation mode.

16. A method for providing spinal cord electrostimulation for pain control in a patient, the method comprising:
receiving information about placement of at least one lead in a vicinity of a lateral portion of a spinal cord;
defining one or more lead electrode-tissue contact groups on the lateral portion of the spinal cord, the one or more contact groups each comprising one or more lateral spinal neural targets identified and grouped based on the information about placement of at least one lead using a programming device;
receiving a user selection from selectable stimulation modes for stimulating the identified one or more lateral spinal neural targets of at least one of the one or more contact groups; and
applying electrostimulation energy generated by an electrostimulator to the identified one or more lateral spinal neural targets via the at least one lead in accordance with the user selection from the selectable stimulation modes.

17. The method of claim 16, wherein the one or more contact groups include at least one of: a first contact group comprising first lateral spinal neural targets, including dorsal column, dorsal rootlets, a dorsal root entry zone, a Lissauer's track, and inhibitory interneurons; a second contact group comprising second lateral spinal neural targets, including one or more midline dorsal roots; or a third contact group comprising third lateral spinal neural targets, including one or more lateral dorsal roots.

18. The method of claim 17, comprising receiving information about pain area on patient body, the pain area corresponding to one or more dermatomes,
wherein the one or more lateral spinal neural targets for at least one of the one or more contact groups is identified further based on a rostral-caudal position or a medio-lateral position of the at least one contact group relative to spinal cord levels innervating the one or more dermatomes corresponding to the pain area.

* * * * *